(12) United States Patent
Ertl et al.

(10) Patent No.: US 7,132,262 B2
(45) Date of Patent: Nov. 7, 2006

(54) PAPILLOMA VIRUS SEQUENCES

(75) Inventors: Peter Franz Ertl, Stevenage (GB); Gerald Wayne Gough, Stevenage (GB); Christopher Jeffrey Alan Ring, Stevenage (GB); Vanita Parmar, Stevenage (GB); Sarah Marina Walcott, Stevenage (GB)

(73) Assignee: SmithKline Beecham Corp., Philadelphia, PA (US)

( * ) Notice: Subject to any disclaimer, the term of this patent is extended or adjusted under 35 U.S.C. 154(b) by 297 days.

(21) Appl. No.: 10/630,880

(22) Filed: Jul. 30, 2003

(65) Prior Publication Data

US 2005/0037337 A1    Feb. 17, 2005

Related U.S. Application Data

(63) Continuation of application No. 09/939,471, filed on Aug. 24, 2001, which is a continuation-in-part of application No. PCT/GB01/03290, filed on Jul. 20, 2001.

(30) Foreign Application Priority Data

Jul. 21, 2000    (GB) ................................ 0017990.3

(51) Int. Cl.
    *C12P 21/06*    (2006.01)
(52) U.S. Cl. .......................................... 435/69.1; 435/6
(58) Field of Classification Search .................. 435/6, 435/69.1, 91.1
    See application file for complete search history.

(56) References Cited

U.S. PATENT DOCUMENTS

| | | | |
|---|---|---|---|
| 5,786,464 A | | 7/1998 | Seed |
| 6,114,148 A | | 9/2000 | Seed et al. |
| 6,290,965 B1 | * | 9/2001 | Jansen et al. ............ 424/199.1 |
| 6,306,580 B1 | * | 10/2001 | Pelletier et al. ................ 435/5 |
| 2005/0075303 A1 | * | 4/2005 | Neeper et al. ................ 514/44 |

FOREIGN PATENT DOCUMENTS

| | | | |
|---|---|---|---|
| EP | 0523395 | | 1/1993 |
| WO | WO92/11290 | | 7/1992 |
| WO | WO 99/57283 | * | 11/1993 |
| WO | WO 97/05164 | * | 2/1997 |
| WO | WO 97/031115 | | 8/1997 |
| WO | WO 97/034640 | | 9/1997 |
| WO | WO 97/048370 | | 12/1997 |
| WO | WO01/14416 | | 3/2001 |
| WO | WO 01/14416 A2 | * | 3/2001 |

OTHER PUBLICATIONS

Osen et al , 2001, Vaccine , vol. 19, pp. 4276-4286.*
Yaegashi et al, Journal of Virology, Apr. 1992, vol. 66, No. 4, pp. 2008-2019.*
Zhou Jian, et al., "Papillomavirus Capsid Protein Expression Level Depends on the Match Between Condon Usage and tRNA Availability", *Journal of Virology*, vol. 73 No. 6:4972-4982, (Jun. 6, 1999).
Dartmann, et al., "The Nucleotide Sequence and Genome Organization of Human Papilloma Virus Type 11", *Virology*, vol. 151: 124-130 (1986).
Schwarz, et al., "DNA Sequence and Genome Organization of Genital Human Papillomavirus Type 6b", *Embo Journal*, vol. 2, No. 12: 2341-2348, (1983).
Gouy, et al., "Condon Usage In Bacteria Correlation With Gene Expressively", *Nucleic Acids Research*, vol. 10, No. 22: 7055-7074, (1982).
Hale, et al., "Condon Optimization of the Gene Encoding a Domain From Human Type 1 Neurofibromin Protein Results in a Threefold Improvement in Expression Level in *Escherichia coli*", *Protein Expression and Purification*, vol. 12: 185-188, (Mar. 1998).
Han, et al., "Protection of Rabbits from Viral Challenge by Gene Gun-Based Intracutaneous Vaccination with a Combination of Cottontail Rabbit Papillomavirus E1, E2, E6 and E7 Genes," *Journal of Virology*, vol. 73, No. 8: pp. 7039-7043, (1999).

* cited by examiner

*Primary Examiner*—Ali R. Salimi
(74) *Attorney, Agent, or Firm*—William T. Han; Edward R. Gimmi; Charles M. Kinzig

(57) ABSTRACT

The present invention relates to methods and compositions useful in the treatment and prevention of human papilloma virus infections and the symptoms and diseases associated therewith. More particularly, the invention relates to polynucleotide sequences which encode human papilloma virus (HPV) amino acid amino acid sequences, wherein the codon usage pattern of the polynucleotide sequences resemble those of highly expressed mammalian genes.

16 Claims, 14 Drawing Sheets

Fig. 1

```
           1                                                              60
Hpv11-e1   MADDSGTENEGSGCTGWFMVEAIVEHTTGTQISEDEEEEVEDSGYDMVDFIDDRHITQNS
Hpv6a-e1   MADDSGTENEGSGCTGWFMVEAIVQHPTGTQISDDEDEEVEDSGYDMVDFIDDSNITHNS
    6b-e1  MADDSGTENEGSGCTGWFMVEAIVQHPTGTQISDDEDEEVEDSGYDMVDFIDDSNITHNS 61                                                            120
Hpv11-e1   VEAQALFNRQEADAHYATVQDLKRKYLGSPYVSPISNVANAVESEISPRLDAIKLTTQPK
Hpv6a-e1   LEAQALFNRQEADTHYATVQDLKRKYLGSPYVSPINTIAEAVESEISPRLDAIKLTRQPK
    6b-e1  LEAQALFNRQEADTHYATVQDLKRKYLGSPYVSPINTIAEAVESEISPRLDAIKLTRQPK 121                                                           180
Hpv11-e1   KVKRRLFETRELTDSGYGYSEVEA..ATQVEKHGDPENGGDGQERDTGRDIEGEGVEHRE
Hpv6a-e1   KVKRRLFQTRELTDSGYGYSEVEAGTGTQVEKHGVPENGGDGQEKDTGRDIEG..EEHTE
    6b-e1  KVKRRLFQTRELTDSGYGYSEVEAGTGTQVEKHGVPENGGDGQEKDTGRDIEG..EEHTE 181                                                           240
Hpv11-e1   AEAVDDSTREHADTSGILELLKCKDIRSTLHGKFKDCFGLSFVDLIRPFKSDRTTCADWV
Hpv6a-e1   AEAPTNSVREHAGTAGILELLKCKDLRAALLGKFKECFGLSFIDLIRPFKSDKTTCADWV
    6b-e1  AEAPTNSVREHAGTAGILELLKCKDLRAALLGKFKECFGLSFIDLIRPFKSDKTTCLDWV 241                                                           300
Hpv11-e1   VAGFGIHHSIADAFQKLIEPLSLYAHIQWLTNAWGMVLLVLIRFKVNKSRCTVARTLGTL
Hpv6a-e1   VAGFGIHHSISEAFQKLIEPLSLYAHIQWLTNAWGMVLLVLVRFKVNKSRSTVARTLATL
    6b-e1  VAGFGIHHSISEAFQKLIEPLSLYAHIQWLTNAWGMVLLVLLRFKVNKSRSTVARTLATL 301                                                           360
Hpv11-e1   LNIPENHMLIEPPKIQSGVRALYWFRTGISNASTVIGEAPEWITRQTVIEHSLADSQFKL
Hpv6a-e1   LNIPDNQMLIEPPKIQSGVAALYWFRTGISNASTVIGEAPEWITRQTVIEHGLADSQFKL
    6b-e1  LNIPENQMLIEPPKIQSGVAALYWFRTGISNASTVIGEAPEWITRQTVIEHGLADSQFKL 361                                                           420
Hpv11-e1   TEMVQWAYDNDICEESEIAFEYAQRGDFDSNARAFLNSNMQAKYVKDCAIMCRHYKHAEM
Hpv6a-e1   TEMVQWAYDNDICEESEIAFEYAQRGDFDSNARAFLNSNMQAKYVKDCATMCRHYKHAEM
    6b-e1  TEMVQWAYDNDICEESEIAFEYAQRGDFDSNARAFLNSNMQAKYVKDCATMCRHYKHAEM 421                                                           480
Hpv11-e1   KKMSIKQWIKYRGTKVDSVGNWKPIVQFLRHQNIEFIPFLSKLKLWLHGTPKKNCIAIVG
Hpv6a-e1   RKMSIKQWIKHRGSKIEGTGNWKPIVQFLRHQNIEFIPFLSKFKLWLHGTPKKNCIAIVG
    6b-e1  RKMSIKQWIKHRGSKIEGTGNWKPIVQFLRHQNIEFIPFLTKFKLWLHGTPKKNCIAIVG 481                                                           540
Hpv11-e1   PPDTGKSCFCMSLIKFLGGTVISYVNSCSHFWLQPLTDAKVALLDDATQPCWTYMDTYMR
Hpv6a-e1   PPDTGKSYFCMSLISFLGGTVISHVNSSSHFWLQPLVDAKVALLDDATQPCWIYMDTYMR
    6b-e1  PPDTGKSYFCMSLISFLGGTVISHVNSSSHFWLQPLVDAKVALLDDATQPCWIYMDTYMR 541                                                           600
Hpv11-e1   NLLDGNPMSIDRKHRALTLIKCPPLLVTSNIDISKEEKYKYLHSRVTTFTFPNPFPFDRN
Hpv6a-e1   NLLDGNPMSIDRKHKALTLIKCPPLLVTSNIDITKEEKYKYLHTRVTTFTFPNPFPFDRN
    6b-e1  NLLDGNPMSIDRKHKALTLIKCPPLLVTSNIDITKEDKYKYLHTRVTTFTFPNPFPFDRN 601                             651
Hpv11-e1   GNAVYELSDANWKCFFERLSSSLDIEDSEDEEDGSNSQAFRCVPGSVVRTL  [SEQ.ID NO.1]
Hpv6a-e1   GNAVYELSNANWKCFFERLSSSLDIQDSEDEEDGSNSQAFRCVPGTVVRTL  [SEQ.ID NO.2]
    6b-e1  GNAVYELSNTNWKCFFERLSSSLDIQDSEDEEDGSNSQAFRCVPGTVVRTL  [SEQ.ID NO.3]
```

Fig. 2

```
              1                                                            60
6b-e1         MADDSGTENEGSGCTGWFMVEAIVQHPTGTQISDDEDEEVEDSGYDMVDFIDDSNITHNS
6b-e1 mut     MADDSGTENEGSGCTGWFMVEAIVQHPTGTQISDDEDEEVEDSGYDMVDFIDDSNITHNS 61                                                           120
6b-e1         LEAQALFNRQEADTHYATVQDLKRKYLGSPYVSPINTIAEAVESEISPRLDAIKLTRQPK
6b-e1 mut     LEAQALFNRQEADTHYATVQDLGGKYLGSPYVSPINTIAEAVESEISPRLDAIKLTRQPK 121                                                          180
6b-e1         KVKRRLFQTRELTDSGYGYSEVEAGTGTQVEKHGVPENGGDGQEKDTGRDIEGEEHTEAE
6b-e1 mut     KVKRRLFQTRELTDSGYGYSEVEAGTGTQVEKHGVPENGGDGQEKDTGRDIEGEEHTEAE 181                                                          240
6b-e1         APTNSVREHAGTAGILELLKCKDLRAALLGKFKECFGLSFIDLIRPFKSDKTTCLDWVVA
6b-e1 mut     APTNSVREHAGTAGILELLKCKDLRAALLGKFKECFGLSFIDLIRPFKSDKTTCLDWVVA 241                                                          300
6b-e1         GFGIHHSISEAFQKLIEPLSLYAHIQWLTNAWGMVLLVLLRFKVNKSRSTVARTLATLLN
6b-e1 mut     GFGIHHSISEAFQKLIEPLSLYAHIQWLTNAWGMVLLVLLRFKVNKSRSTVARTLATLLN 301                                                          360
6b-e1         IPENQMLIEPPKIQSGVAALYWFRTGISNASTVIGEAPEWITRQTVIEHGLADSQFKLTE
6b-e1 mut     IPENQMLIEPPKIQSGVAALYWFRTGISNASTVIGEAPEWITRQTVIEHGLADSQFKLTE 361                                                          420
6b-e1         MVQWAYDNDICEESEIAFEYAQRGDFDSNARAFLNSNMQAKYVKDCATMCRHYKHAEMRK
6b-e1 mut     MVQWAYDNDICEESEIAFEYAQRGDFDSNARAFLNSNMQAKYVKDCATMCRHYKHAEMRK 421                                                          480
6b-e1         MSIKQWIKHRGSKIEGTGNWKPIVQFLRHQNIEFIPFLTKFKLWLHGTPKKNCIAIVGPP
6b-e1 mut     MSIKQWIKHRGSKIEGTGNWKPIVQFLRHQNIEFIPFLTKFKLWLHGTPKKNCIAIVGPP 481                                                          540
6b-e1         DTGKSYFCMSLISFLGGTVISHVNSSSHFWLQPLVDAKVALLDDATQPCWIYMDTYMRNL
6b-e1 mut     DTDKSYFCMSLISFLGGTVISHVNSSSHFWLQPLVDAKVALLDDATQPCWIYMDTYMRNL 541                                                          600
6b-e1         LDGNPMSIDRKHKALTLIKCPPLLVTSNIDITKEDKYKYLHTRVTTFTFPNPFPFDRNGN
6b-e1 mut     LDGNPMSIDRKHKALTLIKCPPLLVTSNIDITKEDKYKYLHTRVTTFTFPNPFPFDRNGN 601                                        649
6b-e1         AVYELSNTNWKCFFERLSSSLDIQDSEDEEDGSNSQAFRCVPGTVVRTL   [SEQ.ID NO.4]
6b-e1 mut     AVYELSNTNWKCFFERLSSSLDIQDSEDEEDGSNSQAFRCVPGTVVRTL   [SEQ.ID NO.5]
```

Fig. 3

```
            1                                                           60
Hpv-11e2    MEAIAKRLDACQDQLLELYEENSIDIHKHIMHWKCIRLESVLLHKAKQMGLSHIGLQVVP
Hpv6a-e2    MEAIAKRLDACQEQLLELYEENSTDLNKHVLHWKCMRHESVLLYKAKQMGLSHIGMQVVP
Hpv6b-e2    MEAIAKRLDACQEQLLELYEENSTDLHKHVLHWKCMRHESVLLYKAKQMGLSHIGMQVVP 61                                                          120
Hpv-11e2    PLTVSETKGHNAIEMQMHLESLAKTQYGVEPWTLQDTSYEMWLTPPKRCFKKQGNTVEVK
Hpv6a-e2    PLKVSEAKGHNAIEMQMHLESLLKTEYSMEPWTLQETSYEMWQTPPKRCFKKRGKTVEVK
Hpv6b-e2    PLKVSEAKGHNAIEMQMHLESLLRTEYSMEPWTLQETSYEMWQTPPKRCFKKRGKTVEVK 121                                                         180
Hpv-11e2    FDGCEDNVMEYVVWTHIYLQDNDSWVKVTSSVDAKGIYYTCGQFKTYYVNFNKEAQKYGS
Hpv6a-e2    FDGCANNTMDYVVWTDVYVQDTDSWVKVHSMVDAKGIYYTCGQFKTYYVNFVKEAEKYGS
Hpv6b-e2    FDGCANNTMDYVVWTDVYVQDNDTWVKVHSMVDAKGIYYTCGQFKTYYVNFVKEAEKYGS 181                                                         240
Hpv-11e2    TNHWEVCYGSTVICSPASVSSTVREVSIAEPTTYTPAQTTAPTVSACTTEDGVSAPPRKR
Hpv6a-e2    TKQWEVCYGSTVICSPASVSSTTQEVSIPESTTYTPAQTSTP.VSSSTQEDAVQTPPRKR
Hpv6b-e2    TKHWEVCYGSTVICSPASVSSTTQEVSIPESTTYTPAQTSTL.VSSSTKEDAVQTPPRKR 241                                                         300
Hpv-11e2    ARGPSTN..NTLCVANIRSVDSTINNIVTDNYNKHQRRNNCHSAATPIVQLQGDSNCLKC
Hpv6a-e2    ARGVQQSPCNALCVAHIGPVDSGNHNLITNNHDQHQRRNNSNSSATPIVQFQGESNCLKC
Hpv6b-e2    ARGVQQSPCNALCVAHIGPVDSGNHNLITNNHDQHQRRNNSNSSATPIVQFQGESNCLKC 301                                                         360
Hpv-11e2    FRYRLNDKYKHLFELASSTWHWASPEAPHKNAIVTLTYSSEEQRQQFLNSVKIPPTIRHK
Hpv6a-e2    FRYRLNDKHRHLFDLISSTWHWASPKAPHKHAIVTVTYHSEEQRQQFLNVVKIPPTIRHK
Hpv6b-e2    FRYRLNDRHRHLFDLISSTWHWASSKAPHKHAIVTVTYDSEEQRQQFLDVVKIPPTISHK 361     369
Hpv-11e2    VGFMSLHLL  [SEQ. ID NO. 6]
Hpv6a-e2    LGFMSLHLL  [SEQ. ID NO. 7]
Hpv6b-e2    LGFMSLHLL  [SEQ. ID NO. 8]
```

Fig. 4a

```
                 1                                                            60
Hpv-11e2-comut   MEAIAKRLDACQDQLLELYEENSIDIHKHIMHWKCIRLESVLLHKAKQMGLSHIGLQVVP
Hpv-11e2-mut     MEAIAKRLDACQDQLLELYEENSIDIHKHIMHWKCIRLESVLLHKAKQMGLSHIGLQVVP
Hpv-11e2-wt      MEAIAKRLDACQDQLLELYEENSIDIHKHIMHWKCIRLESVLLHKAKQMGLSHIGLQVVP 61                                                           120
Hpv-11e2-comut   PLTVSETKGHNAIEMQMHLESLAKTQYGVEPWTLQDTSYEMWLTPPKRCFAKQGNTVEVK
Hpv-11e2-mut     PLTVSETKGHNAIEMQMHLESLAKTQYGVEPWTLQDTSYEMWLTPPKRCFAKQGNTVEVK
Hpv-11e2-wt      PLTVSETKGHNAIEMQMHLESLAKTQYGVEPWTLQDTSYEMWLTPPKRCFKKQGNTVEVK 121                                                          180
Hpv-11e2-comut   FDGCEDNVMEYVVWTHIYLQDNDSWVKVTSSVDAKGIYYTCGQFKTYYVNFNKEAQKYGS
Hpv-11e2-mut     FDGCEDNVMEYVVWTHIYLQDNDSWVKVTSSVDAKGIYYTCGQFKTYYVNFNKEAQKYGS
Hpv-11e2-wt      FDGCEDNVMEYVVWTHIYLQDNDSWVKVTSSVDAKGIYYTCGQFKTYYVNFNKEAQKYGS 181                                                          240
Hpv-11e2-comut   TNHWEVCYGSTVICSPASVSSTVREVSIAEPTTYTPAQTTAPTVSACTTEDGVSAPPRKR
Hpv-11e2-mut     TNHWEVCYGSTVICSPASVSSTVREVSIAEPTTYTPAQTTAPTVSACTTEDGVSAPPRKR
Hpv-11e2-wt      TNHWEVCYGSTVICSPASVSSTVREVSIAEPTTYTPAQTTAPTVSACTTEDGVSAPPRKR 241                                                          300
Hpv-11e2-comut   ARGPSTNNTLCVANIRSVDSTINNIVTDNYNKHQRRNNCHSAATPIVQLQGDSNCLKCFR
Hpv-11e2-mut     ARGPSTNNTLCVANIRSVDSTINNIVTDNYNKHQRRNNCHSAATPIVQLQGDSNCLKCFR
Hpv-11e2-wt      ARGPSTNNTLCVANIRSVDSTINNIVTDNYNKHQRRNNCHSAATPIVQLQGDSNCLKCFR 301                                                          360
Hpv-11e2-comut   YRLNDKYKHLFELASSTWHWASPEAPHKNAIVTLTYSSEEQRQQFLNSVKIPPTIRHKVG
Hpv-11e2-mut     YRLNDKYKHLFELASSTWHWASPEAPHKNAIVTLTYSSEEQRQQFLNSVKIPPTIRHKVG
Hpv-11e2-wt      YRLNDKYKHLFELASSTWHWASPEAPHKNAIVTLTYSSEEQRQQFLNSVKIPPTIRHKVG 361     367
Hpv-11e2-comut   FMSLHLL  [SEQ. ID NO. 9]
Hpv-11e2-mut     FMSLHLL  [SEQ. ID NO. 10]
Hpv-11e2-wt      FMSLHLL  [SEQ. ID NO. 11]
```

Fig. 4b

```
            1                                                              60
Hpv-6be2-wt   MEAIAKRLDACQEQLLELYEENSTDLHKHVLHWKCMRHESVLLYKAKQMGLSHIGMQVVP
Hpv-6be2-mut  MEAIAKRLDACQEQLLELYEENSTDLHKHVLHWKCMRHESVLLYKAKQMGLSHIGMQVVP 61                                                             120
Hpv-6be2-wt   PLKVSEAKGHNAIEMQMHLESLLRTEYSMEPWTLQETSYEMWQTPPKRCFKKRGKTVEVK
Hpv-6be2-mut  PLKVSEAKGHNAIEMQMHLESLLRTEYSMEPWTLQETSYEMWQTPPKRCFAKRGKTVEVK 121                                                            180
Hpv-6be2-wt   FDGCANNTMDYVVWTDVYVQDNDTWVKVHSMVDAKGIYYTCGQFKTYYVNFVKEAEKYGS
Hpv-6be2-mut  FDGCANNTMDYVVWTDVYVQDNDTWVKVHSMVDAKGIYYTCGQFKTYYVNFVKEAEKYGS 181                                                            240
Hpv-6be2-wt   TKHWEVCYGSTVICSPASVSSTTQEVSIPESTTYTPAQTSTL.VSSSTKEDAVQTPPRKR
Hpv-6be2-mut  TKHWEVCYGSTVICSPASVSSTTQEVSIPESTTYTPAQTSTL.VSSSTKEDAVQTPPRKR 241                                                            300
Hpv-6be2-wt   ARGVQQSPCNALCVAHIGPVDSGNHNLITNNHDQHQRRNNSNSSATPIVQFQGESNCLKC
Hpv-6be2-mut  ARGVQQSPCNALCVAHIGPVDSGNHNLITNNHDQHQRRNNSNSSATPIVQFQGESNCLKC 301                                                            360
Hpv-6be2-wt   FRYRLNDRHRHLFDLISSTWHWASSKAPHKHAIVTVTYDSEEQRQQFLDVVKIPPTISHK
Hpv-6be2-mut  FRYRLNDRHRHLFDLISSTWHWASSKAPHKHAIVTVTYDSEEQRQQFLDVVKIPPTISHK 361     369
Hpv-6be2-wt   LGFMSLHLL   [SEQ. ID NO. 12]
Hpv-6be2-mut  LGFMSLHLL   [SEQ. ID NO. 13]
```

Fig. 5a

```
                    1                                                          60
HPV6be1-comut  GCGGCCGCCATGGCAGACGATTCCGGTACTGAGAACGAAGGTTCTGGTTGTACCGGTTGG 61                                                         120
HPV6be1-comut  TTCATGGTTGAAGCAATCGTTCAGCATCCGACTGGTACCCAGATCTCCGATGACGAAGAC 121                                                        180
HPV6be1-comut  GAAGAAGTTGAAGATTCTGGTTACGACATGGTTGACTTCATCGATGACTCCAACATCACT 181                                                        240
HPV6be1-comut  CATAACTCTCTGGAAGCACAGGCTCTGTTTAACCGCCAGGAAGCTGATACCCATTACGCT 241                                                        300
HPV6be1-comut  ACTGTTCAGGACCTGGGAGGCAAATATCTGGGCTCTCCGTACGTTTCCCCGATCAACACT 301                                                        360
HPV6be1-comut  ATCGCAGAAGCAGTTGAGTCTGAAATCTCCCCGCGCCTGGACGCTATCAAACTGACTCGT 361                                                        420
HPV6be1-comut  CAGCCGAAGAAGGTTAAACGTCGTCTGTTCCAGACTCGTGAACTGACCGACTCCGGTTAC 421                                                        480
HPV6be1-comut  GGTTATAGCGAAGTTGAGGCTGGCACCGGCACCCAGGTTGAAAAACACGGTGTACCGGAA 481                                                        540
HPV6be1-comut  AACGGCGGCGACGGTCAGGAAAAGGACACCGGCCGCGACATCGAGGGTGAGGAACACACC 541                                                        600
HPV6be1-comut  GAAGCTGAAGCTCCGACTAACTCTGTTCGTGAACACGCAGGTACTGCGGGTATCCTGGAA 601                                                        660
HPV6be1-comut  CTGCTGAAATGCAAAGACCTGCGCGCGGCTCTGCTGGGCAAATTCAAAGAATGCTTCGGC 661                                                        720
HPV6be1-comut  CTGTCTTTCATTGACCTGATCCGTCCGTTTAAGTCTGACAAAACTACCTGTCTGGACTGG 721                                                        780
HPV6be1-comut  GTTGTAGCAGGCTTCGGCATCCACCACTCTATCTCTGAAGCATTCCAGAAACTGATCGAG 781                                                        840
HPV6be1-comut  CCGCTGTCTCTGTACGCGCACATCCAGTGGCTGACTAACGCTTGGGGTATGGTTCTGCTG 841                                                        900
HPV6be1-comut  GTACTGCTGCGCTTTAAAGTAAACAAATCTCGTTCCACTGTTGCTCGTACTCTGGCTACC 901                                                        960
HPV6be1-comut  CTGCTGAACATCCCGGAGAACCAGATGCTGATCGAACCGCCGAAAATCCAGTCTGGTGTA 961                                                       1020
HPV6be1-comut  GCTGCACTGTACTGGTTTCGTACTGGCATCTCTAACGCTAGCACTGTTATCGGTGAAGCA 1021                                                       1080
HPV6be1-comut  CCGGAATGGATCACTCGTCAGACCGTTATCGAACACGGTCTGGCAGATTCTCAGTTCAAA 1081                                                       1140
HPV6be1-comut  CTGACTGAAATGGTTCAGTGGGCATACGACAACGACATCTGCGAGGAATCTGAAATTGCG
```

Fig. 5b

```
                            1141                                                           1200
HPV6be1-comut   TTCGAATACGCTCAGCGTGGCGACTTCGACTCCAACGCTCGTGCTTTCCTGAACAGCAAC 1201                                                           1260
HPV6be1-comut   ATGCAGGCTAAATACGTAAAAGACTGCGCTACCATGTGCCGTCACTACAAACACGCGGAA 1261                                                           1320
HPV6be1-comut   ATGCGTAAAATGTCTATCAAACAGTGGATCAAGCACCGCGGTTCTAAAATCGAAGGTACC 1321                                                           1380
HPV6be1-comut   GGTAACTGGAAACCGATCGTTCAGTTCCTGCGCCATCAGAACATCGAATTCATCCCGTTC 1381                                                           1440
HPV6be1-comut   CTGACCAAATTCAAGCTGTGGCTGCACGGTACCCCGAAAAAAAACTGCATCGCTATCGTA 1441                                                           1500
HPV6be1-comut   GGTCCACCGGACACTGACAAGTCTTACTTCTGTATGTCCCTGATCTCTTTCCTGGGCGGC 1501                                                           1560
HPV6be1-comut   ACTGTAATCTCTCACGTTAACTCTTCCTCCCATTTCTGGCTGCAGCCACTGGTAGACGCG 1561                                                           1620
HPV6be1-comut   AAAGTAGCTCTGCTGGACGACGCGACCCAGCCGTGCTGGATCTACATGGATACTTACATG 1621                                                           1680
HPV6be1-comut   CGCAACCTGCTGGACGGTAACCCGATGTCTATCGACCGTAAACACAAAGCGCTGACTCTG 1681                                                           1740
HPV6be1-comut   ATCAAGTGCCCGCCGCTGCTGGTAACTTCTAACATCGACATCACCAAGGAAGATAAATAC 1741                                                           1800
HPV6be1-comut   AAGTACCTGCATACCCGTGTTACTACCTTTACTTTCCCGAACCCGTTCCCGTTTGATCGT 1801                                                           1860
HPV6be1-comut   AACGGTAACGCTGTTTACGAACTGTCCAACACTAACTGGAAATGCTTCTTCGAGCGTCTG 1861                                                           1920
HPV6be1-comut   TCTTCCTCCCTGGACATCCAGGACTCTGAAGATGAAGAAGATGGTTCTAACTCTCAGGCT 1921                                          1968
HPV6be1-comut   TTCCGTTGTGTTCCGGGTACTGTTGTTCGTACTCTGTGAGGATCC''. [SEQ.ID NO. 14]
```

Fig. 6

```
              1                                                           60
Hpv11e2-comut ''GCGGCCGCCATGGAAGCCATCGCGAAGAGGCTCGACGCCTGCCAGGACCAGCTGCTCG 61                                                          120
Hpv11e2-comut AGCTGTACGAGGAGAACAGCATTGACATCCATAAGCACATCATGCACTGGAAGTGCATTC 121                                                         180
Hpv11e2-comut GCCTGGAGAGCGTGCTGTTGCACAAGGCCAAGCAGATGGGCCTGTCCCACATAGGCCTTC 181                                                         240
Hpv11e2-comut AGGTGGTCCCCCCTCTGACCGTGTCAGAGACAAAGGGCCATAACGCAATCGAGATGCAGA 241                                                         300
Hpv11e2-comut TGCACCTCGAGTCGCTGGCGAAAACACAGTACGGCGTGGAGCCATGGACCCTGCAGGACA 301                                                         360
Hpv11e2-comut CCTCGTACGAAATGTGGCTGACCCCACCTAAGCGATGCTTCGCCAAACAGGGCAACACAG 361                                                         420
Hpv11e2-comut TGGAGGTGAAGTTCGACGGCTGTGAGGATAACGTTATGGAGTATGTCGTGTGGACGCACA 421                                                         480
Hpv11e2-comut TCTATCTGCAGGACAACGACAGTTGGGTGAAGGTGACCAGCTCCGTGGACGCGAAGGGCA 481                                                         540
Hpv11e2-comut TCTACTATACCTGTGGGCAGTTTAAAACCTACTATGTGAACTTCAACAAAGAGGCCCAAA 541                                                         600
Hpv11e2-comut AGTATGGCTCCACCAACCACTGGGAGGTCTGCTATGGGAGCACGGTGATTTGCTCTCCCG 601                                                         660
Hpv11e2-comut CCAGCGTGTCTAGCACTGTGCGCGAGGTGAGCATTGCCGAGCCGACCACGTACACCCCTG 661                                                         720
Hpv11e2-comut CCCAGACGACCGCTCCGACCGTGTCTGCTTGTACTACCGAGGACGGCGTGAGCGCTCCAC 721                                                         780
Hpv11e2-comut CCAGGAAGCGTGCGAGGGGCCCAAGCACCAACAACACCCTCTGTGTGGCGAACATTCGCA 781                                                         840
Hpv11e2-comut GCGTCGACAGTACCATCAATAACATCGTGACGGATAACTATAACAAGCACCAGAGGCGTA 841                                                         900
Hpv11e2-comut ACAACTGTCACTCTGCCGCAACCCCCATCGTGCAGCTCCAGGGAGACAGCAATTGCCTTA 901                                                         960
Hpv11e2-comut AGTGCTTCCGCTATCGCCTCAACGACAAGTACAAGCACCTCTTTGAGCTCGCCTCGTCGA 961                                                         1020
Hpv11e2-comut CGTGGCACTGGGCCTCACCCGAGGCACCTCACAAGAACGCCATCGTCACTCTCACTTACT 1021                                                        1080
Hpv11e2-comut CCAGTGAGGAGCAGAGACAGCAGTTTCTGAACAGCGTGAAGATCCCACCGACGATCCGTC 1081                            1123
Hpv11e2-comut ATAAGGTCGGCTTCATGTCACTGC Fig. 7    WRG7313plc
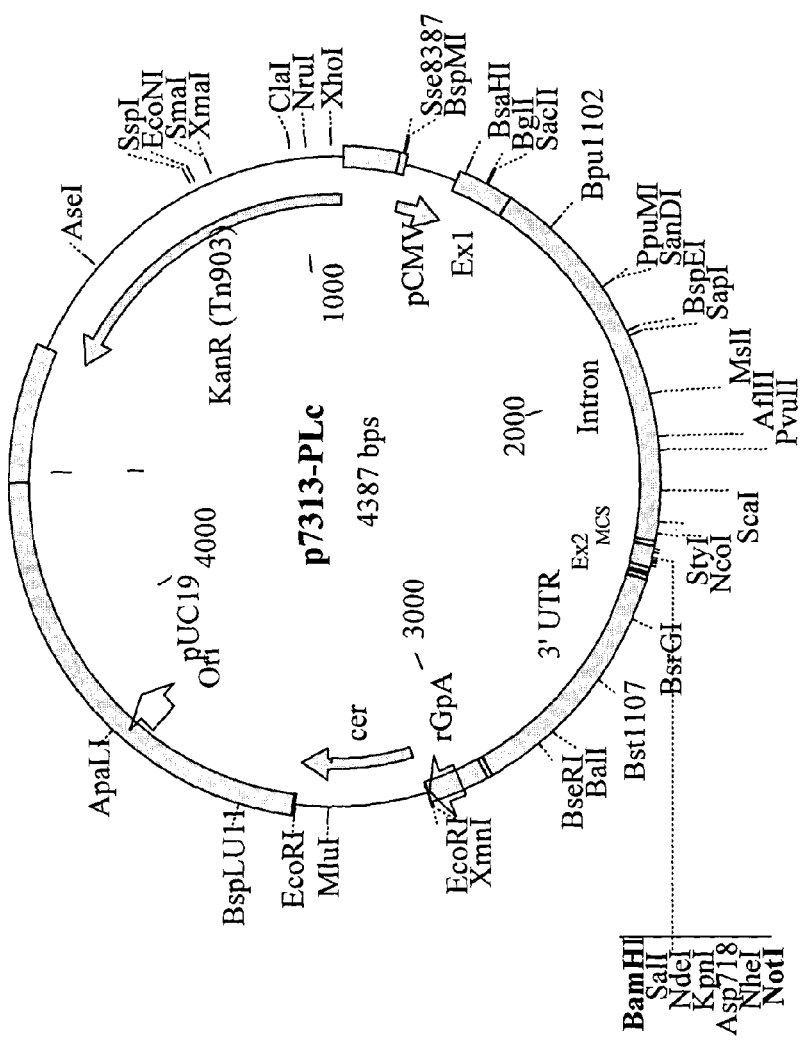

Key:

1- 293T cell lysate control
2- p7313PLc vector control
3- p6bE1 w/t
4- p6bE1 c/o

| | |
|---|---|
| 1 | p7313PLc |
| 2 | p6bE2 w/t |
| 3 | p6bE2 c/o |
| 4 | p6bE2 w/t mutated |
| 5 | p6bE2 c/o mutated |

Fig. 11

Codon-optimised COPV E1 protects against Disease

Fig. 12

Codon-optimisation of the COPV E1 gene significantly improves protein expression.

Key:

A:- Baculovirus COPVE1 lysate
B:- WRG7077 vector
C:- COPVE1 w/t
D:- COPVE1 c/o

A   B   C   D

205 KDa
130 KDa
77 KDa
43 KDa
16 KDa

PAPILLOMA VIRUS SEQUENCES

CROSS REFERENCES TO RELATED APPLICATIONS

This is a contination application of U.S. Ser. No. 09/939,471, filed Aug. 24, 2001, now abandoned which is a continuation-in-part of International Application No.: PCTGB0103290 with an international filing date of 20 Jul. 2001 claiming priority from British patent application No. 0017990.3 (filed 21st Jul. 2000).

The present invention relates to methods and compositions useful in the treatment and prevention of human papilloma virus infections and the symptoms and diseases associated therewith.

Papilloma virus infections have been observed in a variety of species, including sheep, dogs, rabbits, monkeys, cattle and humans. Human papilloma viruses (HPV) have been classified into more than 80 types (Epidemiology and Biology of Cervical Cancer. Seminars in Surgical Oncology 1999 16:203–211). New (novel) types are defined as those where the L1 gene displays less than 90% sequence identity to L1 sequences from previously identified types, whilst a sub-type displays between 90% and 98% L1 sequence identity, and a variant more than 98% sequence identity (to the prototypical (parent) type). Papilloma viruses generally infect epithelia, but the different HPV types cause distinct diseases. For example, types 1–4, 7, 10 and 26–29 cause benign cutaneous warts, types 16, 18, 31, 33, 35, 39, 45, 51, 52, 56, 58, 59, and 68 are associated with cervical cancers and types 6 and 11 are implicated in genital warts (non-malignant condylomata of the genital tract).

The majority of genital warts (>90%) contain HPV genotypes 6 and 11. Whilst HPV-6 is the most prevalent genotype identified in single infections, both HPV-6 and HPV-11 may occasionally occur in the same lesion. Warts generally occur in several sites in infected individuals and more than 60% of patients with partners having condyloma (genital warts) develop lesions, with an average incubation time of 3 months. A range of treatment options are currently available. However, they rely upon excision or ablation and/or the use of topical gels and creams. They are not pain free, they may require frequent clinic visits, and efficacy is highly variable. Disease recurrence remains a significant problem for the effective management of this disease.

Genital warts may regress spontaneously and cell mediated immunity appears to be the primary event responsible for wart regression. The high spontaneous regression rates indicate that host cellular immunity can resolve clinical disease and make immune-therapy intervention an option for treatment or prevention of genital warts. The goals for disease management are for a virus-specific therapy that is pain free, requires a minimum of clinic visits, has high disease resolution rates and which reduces/minimises disease recurrence.

HPV has proven difficult to grow in tissue culture, so there is no traditional live or attenuated viral vaccine. Development of an HPV vaccine has also been slowed by the lack of a suitable animal model in which the human virus can be studied. This is because the viruses are highly species specific, so it is not possible to infect an immunocompetent animal with a human papilloma virus, as would be required for safety testing before a vaccine was first tried in humans.

Papilloma viruses have a DNA genome which encodes "early" and "late" genes designated E1 to E7, L1 and L2. The early gene sequences have been shown to have functions relating to viral DNA replication and transcription, evasion of host immunity, and alteration of the normal host cell cycle and other processes. For example the E1 protein is an ATP-dependent DNA helicase and is involved in initiation of the viral DNA replication process whilst E2 is a regulatory protein controlling both viral gene expression and DNA replication. Through its ability to bind to both E1 and the viral origin of replication, E2 brings about a local concentration of E1 at the origin, thus stimulating the initiation of viral DNA replication. The E4 protein appears to have a number of poorly defined functions but amongst these may be binding to the host cell cytoskeleton, whilst E5 appears to delay acidification of endosomes resulting in increased expression of EGF receptor at the cell surface and both E6 and E7 are known to bind cell proteins p53 and pRB respectively. The E6 and E7 proteins form HPV types associated with cervical cancer are known oncogenes. L1 and L2 encode the two viral structural (capsid) proteins.

Historically, vaccines have been seen as a way to prevent infection by a pathogen, priming the immune system to recognise the pathogen and neutralise it should an infection occur. The vaccine includes one or more antigens from the pathogen, commonly the entire organism, either killed or in a weakened (attenuated) form, or selected antigenic peptides from the organism. When the immune system is exposed to the antigen(s), cells are generated which retain an immunological "memory" of it for the lifetime of the individual. Subsequent exposure to the same antigen (e.g. upon infection by the pathogen) stimulates a specific immune response which results in elimination or inactivation of the infectious agent.

There are two arms to the immune response: a humoral (antibody) response and a cell-mediated response. Protein antigens derived from pathogens that replicate intracellularly (viruses and some bacteria) are processed within the infected host cell releasing short peptides which are subsequently displayed on the infected cell surface in association with class I major histocompatability (MHC I) molecules. When this associated complex of MHC I and peptide is contacted by antigen-specific CD8+ T-cells the T-cell is activated, acquiring cytotoxic activity. These cytotoxic T-cells (CTLs) can lyse infected host cells, so limiting the replication and spread of the infecting pathogen. Another important arm of the immune response is controlled by CD4+ T-cells. When antigen derived from pathogens is released into the extracellular milieu they may be taken up by specialised antigen-presenting cells (APCs) and displayed upon the surface of these cells in association with MHC II molecules. Recognition of antigen in this complex stimulates CD4+ T-cells to secrete soluble factors (cytokines) which regulate the effector mechanisms of other T-cells. Antibody is produced by B-cells. Binding of antigen to secreted antibody may neutralise the infectivity of a pathogen and binding of antigen to membrane-bound antibody on the surface of B-cells stimulates division of the B-cell so amplifying the B-cell response. In general, both antibody and cell-mediated immune responses (CD8+ and CD4+) are required to control infections by pathogens.

It is believed that it may be possible to harness the immune system, even after infection by a pathogen, to control or resolve the infection by inactivation or elimination of the pathogen. Such immune therapies (also known as "therapeutic" vaccines or immunotherapeutics) would ideally require a cell-mediated response to be effective, although both humoral and cell-mediated immune responses may be evoked.

It has been demonstrated (Benvenisty, N and Reshaf, L. PNAS 83 955-9555) that inoculation of mice with calcium phosphate precipitated DNA results in expression of the peptides encoded by the DNA. Subsequently, intramuscular injection into mice of plasmid DNA which had not been precipitated was shown to result in uptake of the DNA into the muscle cells and expression of the encoded protein. Because expression of the DNA results in production of the encoded pathogen proteins within the host's cells, as in a natural infection, this mechanism can stimulate the cell-mediated immune response required for immune therapies or therapeutic vaccination, so a DNA-based drug could be applied as a prophylactic vaccine or as an immune therapy. DNA vaccines are described in WO90/11092 (Vical, Inc.).

DNA vaccination may be delivered by mechanisms other than intra-muscular injection. For example, delivery into the skin takes advantage of the fact that immune mechanisms are highly active in tissues that are barriers to infection such as skin and mucous membranes. Delivery into skin could be via injection, via jet injector (which forces a liquid into the skin, or underlying tissues including muscles, under pressure) or via particle bombardment, in which the DNA may be coated onto particles of sufficient density to penetrate the epithelium (U.S. Pat. No. 5,371,015). For example, the nucleotide sequences may be incorporated into a plasmid which is coated on to gold beads which are then administered under high pressure into the epidermis, such as, for example, as described in Haynes et al J. Biotechnology 44: 37–42 (1996). Projection of these particles into the skin results in direct transfection of both epidermal cells and epidermal Langerhan cells. Langerhan cells are antigen presenting cells (APC) which take up the DNA, express the encoded peptides, and process these for display on cell surface MHC proteins. Transfected Langerhan cells migrate to the lymph nodes where they present the displayed antigen fragments to lymphocytes, evoking an immune response. Very small amounts of DNA (less than 1 µg, often less than 0.5 µg) are required to induce an immune response via particle mediated delivery into skin and this contrasts with the milligram quantities of DNA known to be required to generate immune responses subsequent to direct intramuscular injection.

The expression and detection of HPV proteins in transfected mammalian cells such as HeLa, 293, or CHO cells has often proved difficult and so for biochemical and immunological studies requiring detectable expression of proteins, or quantities of pure proteins the E. coli, Baculovirus or Yeast protein expression systems are often used. In these systems the yields of protein are adequate making functional analysis and purification and subsequent biochemical and immunological studies practicable. However, direct protein detection methods (e.g. Western blotting) typically fail to detect E1 protein expression in transfected mammalian cells even when vectors with strong promoters such as CMV or SV40 are used. Methods designed to increase E1 protein expression in mammalian cells include cloning the 5' flanking sequences alongside the E1 gene (Remm et al. J. Virol 1999 73, 3062–3070) and amplification of the transfected E1 plasmid vector after transfection (Zou et al. J. Virol 1998 72, 3436–3441). Amplification of the input vector plasmid by replication after transfection has the net effect of increasing the E1 gene copy number in the cell, hence boosting protein levels and so facilitating detection of protein (by Western blotting). Because E1 protein expression and detection is problematic in mammalian cells, several authors have resorted to detecting expression of the protein by in vitro transcription-translation with $^{35}$S-labelled methionine using the rabbit reticulocyte system (Promega), (Gopalakrishnan et al. Virology 1999 256, 330–339., Safari et al. Virology 1995 211, 385–396). However, this is a cell-free system and it requires the use of a modified promoter which contains the binding sequence for the RNA polymerase from phage T7.

E1 protein expression has additionally been detected indirectly, via detection of the in vitro DNA replication of a plasmid containing an HPV origin of DNA replication. Detection of this replicated origin containing plasmid acts as a surrogate for E1 (and E2) protein expression (Gopalakrishnan et al, Virology 1999 256, 330–339., Lu et al J. Virol 1993 67, 7131–7139 and Del Vecchio et al J. Virol 1992 66, 5949–5958). Both E1 and E2 are required for replication of the HPV origin, so transfection of mammalian cells with plasmids encoding both the E1 and E2 genes, plus a third plasmid carrying an HPV origin of DNA replication, will only result in replication of the origin carrying plasmid if expression of the E1 protein (and E2 protein) has been successful, albeit undetectable by the standard protein detection method (Western blotting).

The DNA code has 4 letters (A, T, C and G) and uses these to spell three letter "codons" which represent the amino acids of the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons.

Where more than one codon is available to code for a given amino acid, it has been observed that the codon usage patterns of organisms are highly non-random. Different species show a different bias in their codon selection and, furthermore, utilization of codons may be markedly different in a single species between genes which are expressed at high and low levels. This bias is different in viruses, plants, bacteria and mammalian cells, and some species show a stronger bias away from a random codon selection than others. For example, humans and other mammals are less strongly biased than certain bacteria or viruses. For these reasons, there is a significant probability that a mammalian gene expressed in E. coli or a viral gene expressed in mammalian cells will have an inappropriate distribution of codons for efficient expression. However, a gene with a codon usage pattern suitable for E. coli expression may also be efficiently expressed in humans. It is believed that the presence in a heterologous DNA sequence of clusters of codons which are rarely observed in the host in which expression is to occur, is predictive of low heterologous expression levels in that host.

There are several examples where changing codons from those which are rare in the host to those which are host-preferred ("codon optimisation") has enhanced heterologous expression levels, for example the BPV (bovine papilloma virus) late genes L1 and L2 have been codon optimised for mammalian codon usage patterns and this has been shown to give increased expression levels over the wild-type HPV sequences in mammalian (Cos-1) cell culture (Zhou et. al. J. Virol 1999. 73, 4972–4982). In this work, every BPV codon which occurred more than twice as frequently in BPV than in mammals (ration of usage>2), and most codons with a usage ratio of >1.5 were conservatively replaced by the preferentially used mammalian codon. In WO97/31115, WO97/48370 and WO98/34640 (Merck & Co., Inc.) codon optimisation of HIV genes or segments thereof has been shown to result in increased protein expression and improved immunogenicity when the codon optimised sequences are used as DNA vaccines in the host mammal for which the optimisation was tailored. In this work, the sequences consist entirely of optimised codons (except where this would introduce an undesired restriction site, intron splice site etc.) because each viral codon is conservatively replaced with the optimal codon for the intended host.

According to a first aspect, the present invention provides a polynucleotide sequence which encodes an HPV amino acid sequence, wherein the codon usage pattern of the polynucleotide sequence resembles that of highly expressed mammalian genes. Preferably the polynucleotide sequence is a DNA sequence. Desirably the codon usage pattern of the polynucleotide sequence resembles that of highly expressed human genes. Ideally, the codon usage pattern of the polynucleotide sequence also resembles that of highly expressed E. coli genes. The polynucleotide sequence may be a DNA sequence, for example a double stranded DNA sequence. Preferably the polynucleotide sequence encodes a HPV polypeptide of an HPV type or sub-type associated with cervical cancer, benign cutaneous warts or genital warts, for example types, 1–4, 6, 7, 10, 11, 16, 18, 26–29, 31, 33, 35, 39, 45, 51, 52, 56, 58, 59, and 68, preferably types 6, 11, 16, 18, 33 or 45, which are associated particularly with cervical cancer and genital warts, most preferably HPV 11, 6a or 6b.

Accordingly, there is provided a synthetic gene comprising a plurality of codons together encoding an HPV amino acid sequence, wherein the selection of the possible codons used for encoding the amino acid sequence has been changed to resemble the optimal mammalian codon usage such that the frequency of codon usage in the synthetic gene ore closely resembles that of highly expressed mammalian genes than that of papilloma virus genes. Preferably the codon usage pattern is substantially the same as that for highly expressed human genes.

In certain embodiments, the encoded amino acid sequence is a wild-type HPV amino acid sequence. In alternative embodiments, the encoded amino acid sequence is a mutated HPV amino acid sequence comprising the wild-type sequence with amino acid changes, for example amino acid point mutations, sufficient to reduce or inactivate one or more of the natural biological functions of the polypeptide. The mutated amino acid sequence will desirably retain the immunogenicity of the wild-type polypeptide.

The encoded HPV polypeptide may comprise an early gene product such as E1, E2 or E7, or a fragment, analogue or fusion thereof, or may be a late gene product such as L1 or L2, or a fragment, analogue or fusion thereof. A polynucleotide of the invention may for example encode a fusion between two or more HPV early gene products, an HPV early gene product and an HPV late gene product, or between two or more HPV late gene products, between one or more fragments of HPV gene products, or between an HPV gene product (or a fragment thereof) and a polypeptide derived from a source other than HPV, for example an adjuvant or targeting peptide, or polypeptide, such as an HBV core peptide. Fusions may be between HPV gene products derived from the same or different viral types or sub-types. Such fusions will desirably retain the immunogenicity of the fused polypeptide components. Preferably, the encoded HPV polypeptide comprises the whole or a part of an early gene product, most preferably E1 or E2. In one particular embodiment, the polynucleotide sequence encodes the wild-type E1 polypeptide of HPV 6b as set out in FIG. 1, or a fragment or analogue thereof. In alternative embodiments, the polynucleotide sequence may encode one or more of: the mutated HPV6b E1 amino acid sequence set out in FIG. 2; the wild-type E2 amino acid sequence (FIG. 3) of HPV 11 or of 6a or 6b; the mutated HPV6b E2 amino acid sequence of FIG. 4b; and the mutated HPV 11E2 sequence of FIG. 4a, or fragments, analogues or fusions thereof in which the encoded polypeptides retain immunogenicity.

According to the present invention, the codon usage pattern of the polynucleotide will preferably exclude codons with an RSCU value of less than 0.2 in highly expressed genes of the target organism. A relative synonymous codon usage (RSCU) value is the observed number of codons divided by the number expected if all codons for that amino acid were used equally frequently. A polynucleotide of the present invention will generally have a codon usage coefficient (as defined below) for highly expressed human genes of greater than 0.3, preferably greater than 0.4, most preferably greater than 0.5 but less than 1. desirably the polynucleotide will also have a codon usage coefficient for highly expressed E. coli genes of greater than 0.5, preferably greater than 0.6, most preferably greater than 0.7.

In one embodiment, the present invention provides a polynucleotide sequence as set out in FIGS. 5a and 5b or FIG. 6, or a fragment or analogue thereof which maintains the codon usage pattern thereof. In a further embodiment, the present invention provides a polynucleotide sequence complementary to the sequence set out in FIGS. 5a and 5b or FIG. 6.

According to a second aspect of the invention, an expression vector is provided which comprises and is capable of directing the expression of a polynucleotide sequence according to the first aspect of the invention, encoding an HPV amino acid sequence wherein the codon usage pattern of the polynucleotide sequence resembles that of highly expressed mammalian genes, preferably highly expressed human genes. The vector may be suitable for driving expression of heterologous DNA in bacterial insect or mammalian cells, particularly human cells. In one embodiment, the expression vector is p7313PLc (FIG. 7).

According to a third aspect of the invention, a host cell comprising a polynucleotide sequence according to the first aspect of the invention, or an expression vector according the second aspect, is provided. The host cell may be bacterial, e.g. E. coli, mammalian, e.g. human, or may be an insect cell. Mammalian cells comprising a vector according to the present invention may be cultured cells transfected in vitro or may be transfected in vivo by administration of the vector to the mammal.

In a fourth aspect, the present invention provides a pharmaceutical composition comprising a polynucleotide sequence according to the first aspect of the invention. Preferably the composition comprises a DNA vector according to the second aspect of the present invention. In preferred embodiments the composition comprises a plurality of particles, preferably gold particles, coated with DNA comprising a vector encoding a polynucleotide sequence which encodes an HPV amino acid sequence, wherein the codon usage pattern of the polynucleotide sequence resembles that of highly expressed mammalian genes, particularly human genes. In alternative embodiments, the composition comprises a pharmaceutically acceptable excipient and a DNA vector according to the second aspect of the present invention. The composition may also include an adjuvant.

In a further aspect, the present invention provides a method of making a pharmaceutical composition including the step of altering the codon usage pattern of a wild-type HPV nucleotide sequence, or creating a polynucleotide sequence synthetically, to produce a sequence having a codon usage pattern resembling that of highly expressed mammalian genes and encoding a wild-type HPV amino acid sequence or a mutated HPV amino acid sequence comprising the wild-type sequence with amino acid changes sufficient to inactivate one or more of the natural functions of the polypeptide.

Also provided are the use of a polynucleotide according to the first aspect, or of a vector according to a second aspect of the invention, in the treatment or prophylaxis of an HPV infection, preferably an infection by an HPV type or sub-type associated with cervical cancer, benign cutaneous warts or genital warts, for example types, 1–4, 6, 7, 10, 11, 16, 18, 26–29, 31, 33, 35, 39, 45, 51, 52, 56, 58, 59, and 68. In certain embodiments, the invention provides the use of a polynucleotide according to the first aspect, or of a vector according to a second aspect of the invention, in the treatment or prophylaxis of an HPV infection of type 6, 11, 16, 18, 33 or 45, which are associated particularly with cervical cancer and genital warts, most preferably HPV 11, 6a or 6b. The invention also provides the use of a polynucleotide according to the first aspect, a vector according to the second aspect of the invention or a pharmaceutical composition according to the fourth aspect of the invention, in the treatment or prophylaxis of cutaneous (skin) warts, genital warts, atypical squamous cells of undetermined significance (ASCUS), cervical dysplasia, cervical intraepithelial neoplasia (CIN) or cervical cancer. Accordingly, the present invention also provides the use of a polynucleotide according to the first aspect, or of a vector according to the second aspect of the invention in making a medicament for the treatment or prophylaxis of an HPV infection of any one or more of types 1–4, 6, 7, 10, 11, 16, 18, 26–29, 31, 33, 35, 39, 45, 51, 52, 56, 58, 59, and 68, or any symptoms or disease associated therewith.

The present invention also provides methods of treating or preventing HPV infections, particularly infections by any one or more of HPV types 1–4, 6, 7, 10, 11, 16, 18, 26–29, 31, 33, 35, 39, 45, 51, 52, 56, 58, 59, and 68, or any symptoms or diseases associated therewith, comprising administering an effective amount of a polynucleotide according to the first aspect, a vector according to the second aspect or a pharmaceutical composition according to the fourth aspect of the invention. Administration of a pharmaceutical composition may take the form of one or more individual doses, for example in a "prime-boost" therapeutic vaccination regime. In certain cases the "prime" vaccination may be via particle mediated DNA delivery of a polynucleotide according to the present invention, preferably incorporated into a plasmid-derived vector and the "boost" by administration of a recombinant viral vector comprising the same polynucleotide sequence.

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

The term "analogue" refers to a polynucleotide which encodes the same amino acid sequence as another polynucleotide of the present invention but which, through the redundancy of the genetic code, has a different nucleotide sequence whilst maintaining the same codon usage pattern, for example having the same codon usage coefficient or a codon usage coefficient within 0.1, preferably within 0.05 of that of the other polynucleotide.

The term "codon usage pattern" refers to the average frequencies for all codons in the nucleotide sequence, gene or class of genes under discussion (e.g. highly expressed mammalian genes). Codon usage patterns for mammals, including humans can be found in the literature (see e.g. Nakamura et. al. Nucleic Acids Research 1996, 24:214–215).

In the polynucleotides of the present invention, the codon usage pattern is altered from that typical of human papilloma viruses to more closely represent the codon bias of the target organism, e.g. E. coli or a mammal, especially a human. The "codon usage coefficient" is a measure of how closely the codon usage pattern of a given polynucleotide sequence resembles that of a target species. Codon frequencies can be derived from literature sources for the highly expressed genes of many species (see e.g. Nakamura et. al. Nucleic Acids Research 1996, 24:214–215). The codon frequencies for each of the 61 codons (expressed as the number of occurrences occurrence per 1000 codons of the selected class of genes) are normalised for each of the twenty natural amino acids, so that the value for the most frequently used codon for each amino acid is set to 1 and the frequencies for the less common codons are scaled to lie between zero and 1. Thus each of the 61 codons is assigned a value of 1 or lower for the highly expressed genes of the target species. In order to calculate a codon usage coefficient for a specific polynucleotide, relative to the highly expressed genes of that species, the scaled value for each codon of the specific polynucleotide are noted and the geometric mean of all these values is taken (by dividing the sum of the natural logs of these values by the total number of codons and take the anti-log). The coefficient will have a value between zero and 1 and the higher the coefficient the more codons in the polynucleotide are frequently used codons. If a polynucleotide sequence has a codon usage coefficient of 1, all of the codons are "most frequent" codons for highly expressed genes of the target species.

Shorter polynucleotide sequences are within the scope of the invention. For example, a polynucleotide of the invention may encode a fragment of a HPV protein. A polynucleotide which encodes a fragment of at least 8, for example 8–10 amino acids or up to 20, 50, 60, 70, 80, 100, 150 or 200 amino acids in length is considered to fall within the scope of the invention as long as the polynucleotide has a codon usage pattern which resembles that of a highly expressed mammalian gene and the encoded oligo or polypeptide demonstrates HPV antigenicity. In particular, but not exclusively, this aspect of the invention encompasses the situation when the polynucleotide encodes a fragment of a complete HPV protein sequence and may represent one or more discrete epitopes of that protein.

The polynucleotides of the present invention show higher expression in E. coli and mammalian cells than corresponding wild-type sequences encoding the same amino acid sequences. Whilst not wishing to be bound by any theory, this is believed to be for at least two reasons. Firstly, having a codon usage pattern closer to that of the host cell, the sequences are more easily processed by the cell translation machinery. Secondly, as up to 30% of the nucleotide sequence (or more) is different from the wild-type sequence, sites which interfere with transcription or translation (such as protein binding sites) will have been removed or altered.

In some embodiments, polynucleotides according to the present invention show codon usage patterns which resemble those of E. coli and mammalian (e.g. human)

genes. This is particularly advantageous where a sequence is to be used in vaccination of a mammal and in generation of significant amounts of the antigen protein in vitro using *E. coli* cells (e.g. for use in assays, such as immunoassays to judge the levels of expression in mammalian or human tissues).

As discussed above, the present invention includes expression vectors that comprise the nucleotide sequences of the invention. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Other suitable vectors would be apparent to persons skilled in the art. By way of further example in this regard we refer to Sambrook et al. Molecular Cloning: a Laboratory Manual. $2^{nd}$ Edition. CSH Laboratory Press. (1989).

Preferably, a polynucleotide of the invention, or for use in the invention in a vector, is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors may be, for example, plasmids, artificial chromosomes (e.g. BAC, PAC, YAC), virus or phage vectors provided with a origin of replication, optionally a promoter for the expression of the polynucleotide and optionally a regulator of the promoter. The vectors may contain one or more selectable marker genes, for example an ampicillin or kanamycin resistance gene in the case of a bacterial plasmid or a resistance gene for a fungal vector. Vectors may be used in vitro, for example for the production of DNA or RNA or used to transfect or transform a host cell, for example, a mammalian host cell e.g. for the production of protein encoded by the vector. The vectors may also be adapted to be used in vivo, for example in a method of DNA vaccination or of gene therapy.

Promoters and other expression regulation signals may be selected to be compatible with the host cell for which expression is designed. For example, mammalian promoters include the metallothionein promoter, which can be induced in response to heavy metals such as cadmium, and the β-actin promoter. Viral promoters such as the SV40 large T antigen promoter, human cytomegalovirus (CMV) immediate early (IE) promoter, rous sarcoma virus LTR promoter, adenovirus promoter, or a HPV promoter, particularly the HPV upstream regulatory region (URR) may also be used. All these promoters are well described and readily available in the art.

Examples of suitable viral vectors include herpes simplex viral vectors, vaccinia or alpha-virus vectors and retroviruses, including *lentiviruses*, adenoviruses and adeno-associated viruses. Gene transfer techniques using these viruses are known to those skilled in the art. Retrovirus vectors for example may be used to stably integrate the polynucleotide of the invention into the host genome, although such recombination is not preferred. Replication-defective adenovirus vectors by contrast remain episomal and therefore allow transient expression. Vectors capable of driving expression in insect cells (for example baculovirus vectors), in human cells or in bacteria may be employed in order to produce quantities of the HPV protein encoded by the polynucleotides of the present invention, for example for use as subunit vaccines or in immunoassays.

The polynucleotides according to the invention have utility in the production by expression of the encoded proteins, which expression may take place in vitro, in vivo or ex vivo. The nucleotides may therefore be involved in recombinant protein synthesis, for example to increase yields, or indeed may find use as therapeutic agents in their own right, utilised in DNA vaccination techniques. Where the polynucleotides of the present invention are used in the production of the encoded proteins in vitro or ex vivo, cells, for example in cell culture, will be modified to include the polynucleotide to be expressed. Such cells include transient, or preferably stable mammalian cell lines. Particular examples of cells which may be modified by insertion of vectors encoding for a polypeptide according to the invention include mammalian HEK293T, CHO, HeLa, 293 and COS cells. Preferably the cell line selected will be one which is not only stable, but also allows for mature glycosylation and cell surface expression of a polypeptide. Expression may be achieved in transformed oocytes. A polypeptide may be expressed from a polynucleotide of the present invention, in cells of a transgenic non-human animal, preferably a mouse. A transgenic non-human animal expressing a polypeptide from a polynucleotide of the invention is included within the scope of the invention.

Where the polynucleotides of the present invention find use as therapeutic agents, e.g. in DNA vaccination, the nucleic acid will be administered to the mammal e.g. human to be vaccinated. The nucleic acid, such as RNA or DNA, preferably DNA, is provided in the form of a vector, such as those described above, which may be expressed in the cells of the mammal. The polynucleotides may be administered by any available technique. For example, the nucleic acid may be introduced by needle injection, preferably intradermally, subcutaneously or intramuscularly. Alternatively, the nucleic acid may be delivered directly into the skin using a nucleic acid delivery device such as particle-mediated DNA delivery (PMDD). In this method, inert particles (such as gold beads) are coated with a nucleic acid, and are accelerated at speeds sufficient to enable them to penetrate a surface of a recipient (e.g. skin), for example by means of discharge under high pressure from a projecting device. (Particles coated with a nucleic acid molecule of the present invention are within the scope of the present invention, as are delivery devices loaded with such particles). The composition desirably comprises gold particles having an average diameter of 0.5–5 μm, preferably about 2 μm. In preferred embodiments, the coated gold beads are loaded into tubing to serve as cartridges such that each cartridge contains 0.1–1 mg, preferably 0.5 mg gold coated with 0.1–5 μg, preferably about 0.5 μg DNA/cartridge.

Suitable techniques for introducing the naked polynucleotide or vector into a patient include topical application with an appropriate vehicle. The nucleic acid may be administered topically to the skin, or to mucosal surfaces for example by intranasal, oral, intravaginal or intrarectal administration. The naked polynucleotide or vector may be present together with a pharmaceutically acceptable excipient, such as phosphate buffered saline (PBS). DNA uptake may be further facilitated by use of facilitating agents such as bupivacaine, either separately or included in the DNA formulation. Other methods of administering the nucleic acid directly to a recipient include ultrasound, electrical stimulation, electroporation and microseeding which is described in U.S. Pat. No. 5,697,901.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectam and transfectam. The dosage of the nucleic acid to be administered can be altered. Typically the nucleic acid is administered in an amount in the range of 1 pg to 1 mg, preferably 1 pg to 10 µg nucleic acid for particle mediated gene delivery and 10 µg to 1 mg for other routes.

A nucleic acid sequence of the present invention may also be administered by means of specialised delivery vectors useful in gene therapy. Gene therapy approaches are discussed for example by Verme et al, Nature 1997, 389: 239–242. Both viral and non-viral vector systems can be used. Viral based systems include retroviral, lentiviral, adenoviral, adeno-associated viral, herpes viral, Canarypox and vaccinia-viral based systems. Non-viral based systems include direct administration of nucleic acids, microsphere encapsulation technology (poly(lactide-co-glycolide) and, liposome-based systems. Viral and non-viral delivery systems may be combined where it is desirable to provide booster injections after an initial vaccination, for example an initial "prime" DNA vaccination using a non-viral vector such as a plasmid followed by one or more "boost" vaccinations using a viral vector or non-viral based system.

A nucleic acid sequence of the present invention may also be administered by means of transformed cells. Such cells include cells harvested from a subject. The naked polynucleotide or vector of the present invention can be introduced into such cells in vitro and the transformed cells can later be returned to the subject. The polynucleotide of the invention may integrate into nucleic acid already present in a cell by homologous recombination events. A transformed cell may, if desired, be grown up in vitro and one or more of the resultant cells may be used in the present invention. Cells can be provided at an appropriate site in a patient by known surgical or microsurgical techniques (e.g. grafting, microinjection, etc.)

Suitable cells include antigen-presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumour, e.g. anti-cervical carcinoma effects per se and/or to be immunologically compatible with the receiver (i.e., matched HLA haplotype). APCs may generally be isolated from any of a variety of biological fluids and organs, including tumour and peri-tumoural tissues, and may be autologous, allogeneic, syngeneic or xenogeneic cells.

Certain preferred embodiments of the present invention use dendritic cells or progenitors thereof as antigen-presenting cells, either for transformation in vitro and return to the patient or as the in vivo target of nucleotides delivered in the vaccine, for example by particle mediated DNA delivery. Dendritic cells are highly potent APCs (Banchereau and Steinman, Nature 392:245–251, 1998) and have been shown to be effective as a physiological adjuvant for eliciting prophylactic or therapeutic antitumour immunity (see Timmerman and Levy, Ann. Rev. Med. 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, for example the antigen(s) encoded in the constructs of the invention, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594–600, 1998).

Dendritic cells and progenitors may be obtained from peripheral blood, bone marrow, tumour-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNF to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNF, CD40 ligand, lipopolysaccharide LPS, flt3 ligand (a cytokine important in the generation of professional antigen presenting cells, particularly dentritic cells) and/or other compound(s) that induce differentiation, maturation and proliferation of dendritic cells.

APCs may generally be transfected with a polynucleotide encoding an antigenic HPV amino acid sequence, such as a codon-optimised polynucleotide as envisaged in the present invention. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the particle mediated approach described by Mahvi et al., Immunology and cell Biology 75:456–460, 1997.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use. Vaccines comprising nucleotide sequences intended for administration via particle mediated delivery may be presented as cartridges suitable for use with a compressed gas delivery instrument, in which case the cartridges may consist of hollow tubes the inner surface of which is coated with particles bearing the vaccine nucleotide sequence, optionally in the presence of other pharmaceutically acceptable ingredients.

The pharmaceutical compositions of the present invention may include adjuvant compounds, or other substances which may serve to modulate or increase the immune response induced by the protein which is encoded by the DNA. These may be encoded by the DNA, either separately from or as a fusion with the antigen, or may be included as non-DNA elements of the formulation. Examples of adjuvant-type substances which may be included in the formulations of the present invention include ubiquitin, lysosomal associated membrane protein (LAMP), *hepatitis B* virus core antigen, flt3-ligand and other cytokines such as IFN-γ and GMCSF.

Other suitable adjuvants are commercially available such as, for example, Freund's Incomplete Adjuvant and Complete Adjuvant (Difco Laboratories, Detroit, Mich.); Imiquimod (3M, St. Paul, Minn.); Resimiquimod (3M, St. Paul, Minn.); Merck Adjuvant 65 (Merck and Company, Inc., Rahway, N.J.); AS-2 (SmithKline Beecham, Philadelphia, Pa.); aluminium salts such as aluminium hydroxide gel (alum) or aluminium phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

In the formulations of the invention it is preferred that the adjuvant composition induces an immune response predominantly of the Th1 type. Thus the adjuvant may serve to modulate the immune response generated in response to the DNA-encoded antigens from a predominantly Th2 to a predominantly Th1 type response. High levels of Th1-type cytokines (e.g., IFN-, TNF, IL-2 and IL-12) tend to favour the induction of cell mediated immune responses to an administered antigen. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immnunol.* 7:145–173, 1989.

Accordingly, suitable adjuvants for use in eliciting a predominantly Th 1-type response include, for example, a combination of monophosphoryl lipid A, preferably 3-de-O-acylated monophosphoryl lipid A (3D-MPL) together with an aluminium salt. Other known adjuvants which preferentially induce a TH1 type immune response include CpG containing oligonucleotides. The oligonucleotides are characterised in that the CpG dinucleotide is unmethylated. Such oligonucleotides are well known and are described in, for example WO96/02555. Immunostimulatory DNA sequences are also described, for example, by Sato et al., *Science* 273:352, 1996. CpG-containing oligonucleotides may be encoded separately from the papilloma antigen(s) in the same or a different polynucleotide construct, or may be immediately adjacent thereto, e.g. as a fusion therewith. Alternatively the CpG-containing oligonucleotides may be administered separately i.e. not as part of the composition which includes the encoded antigen. CpG oligonucleotides may be used alone or in combination with other adjuvants. For example, an enhanced system involves the combination of a CpG-containing oligonucleotide and a saponin derivative particularly the combination of CpG and QS21 as disclosed in WO 00/09159 and WO 00/62800. Preferably the formulation additionally comprises an oil in water emulsion and/or tocopherol.

Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, Calif., United States), ISCOMS (CSL), MF-59 (Chiron), Detox (Ribi, Hamilton, Mont.), RC-529 (Corixa, Hamilton, Mont.) and other aminoalkyl glucosaminide 4-phosphates (AGPs).

Other preferred adjuvants include adjuvant molecules of the general formula (I)

$$HO(CH_2CH_2O)_n\text{-}A\text{---}R \qquad \text{Formula (I):}$$

wherein, n is 1–50, A is a bond or —C(O)—, R is C1–50 alkyl or Phenyl C1–50 alkyl.

One embodiment of the present invention consists of a formulation comprising a polyoxyethylene ether of general formula (I), wherein n is between 1 and 50, preferably 4–24, most preferably 9; the R component is C1–50, preferably C4—C20 alkyl and most preferably C12 alkyl, and A is a bond. The concentration of the polyoxyethylene ethers should be in the range 0.1–20%, preferably from 0.1–10%, and most preferably in the range 0.1–1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index (12th edition: entry 7717). These adjuvant molecules are described in WO 99/52549. The polyoxyethylene ether according to the general formula (I) above may, if desired, be combined with another adjuvant. For example, a preferred adjuvant combination is preferably with CpG as described in the pending UK patent application GB 9820956.2.

Where the vaccine includes an adjuvant, the vaccine formulation may be administered in two parts. For example, the part of the formulation containing the nucleotide construct which encodes the antigen may be administered first, e.g. by subcutaneous or intramuscular injection, or by intradermal particle-mediated delivery, then the part of the formulation containing the adjuvant may be administered subsequently, either immediately or after a suitable time period which will be apparent to the physician skilled in the vaccines arts. Under these circumstances the adjuvant may be administered by the same route as the antigenic formulation or by an alternate route. In other embodiments the adjuvant part of the formulation will be administered before the antigenic part. In one embodiment, the adjuvant is administered as a topical formulation, applied to the skin at the site of particle mediated delivery of the nucleotide sequences which encode the antigen(s), either before or after the particle mediated delivery thereof.

BRIEF DESCRIPTION OF THE DRAWINGS

The following Examples serve to further illustrate the invention, with reference to the accompanying drawings, in which:

FIG. 1 shows the prototype wild-type amino acid sequences of E1 from Hpv 11, Hpv6a, and Hpv6b, derived from Genbank;

FIG. 2 shows the prototype wild-type amino acid sequence of HPV6b E1 from FIG. 1 (6b-e1) aligned with the HPV6b E1 amino acid sequence including point mutations to remove biological activity (6b-e1 mut);

FIG. 3 shows the prototype wild-type amino acid sequences of E2 from HPV 11, Hpv6a, and Hpv6b, derived from Genbank;

FIG. 4*a* shows the prototype wild-type amino acid sequence of HPV 11 E2 from FIG. 3 (Hpv-11e2-wt) aligned with the HPV 11 E2 amino acid sequence including a point mutation to remove biological activity (Hpv-11e2-mut) and with the amino acid sequence encoded by the nucleotide sequence of FIG. 6 (Hpv-11e2-comut);

FIG. 4*b* shows the prototype wild-type amino acid sequence of HPV6b E2 from FIG. 3 (Hpv-6be2-wt) aligned with the HPV6b E2 amino acid sequence including a point mutation to remove biological activity (Hpv-6be2-mut);

FIGS. 5*a* and 5*b* shows HPV6be1-comut, a nucleotide sequence, having a codon usage pattern resembling that of a highly expressed human gene, encoding the mutated amino acid sequence of HPV6b E1 from FIG. 2;

FIG. 6 shows Hpv11e2-comut, a nucleotide sequence, having a codon usage pattern resembling that of a highly expressed human gene, encoding the mutated amino acid sequence of HPV11 E2 from FIG. 4;

FIG. 7 shows DNA vector p7313-PLc;

FIG. 11 shows a polyacryamide gel demonstrating the improved expression of codon optimised E1.

FIG. 12 shows the protective efficacy of codon optimised E1 in the dog model.

EXAMPLE 1

Codon Optimisation of HPV6bE1

Figure 8:
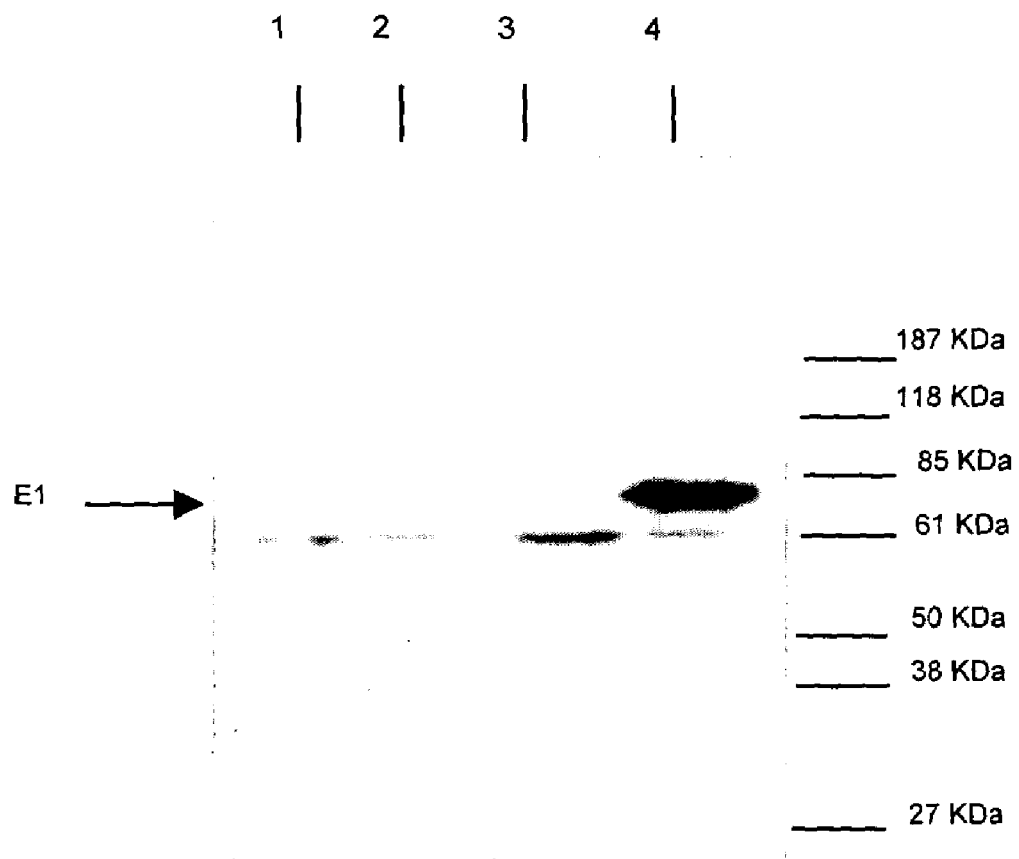
FIG. 8 shows cell lysate samples from Example 4 run on an acrylamide gel and stained to show antibody binding to expressed E1 protein.

The wild-type prototype amino acid sequence of HPV6b E1, obtained from Genbank, is set out in FIG. 1 (bottom sequence). This figure shows the high level of homology for this protein between the HPV virus prototype sequences of types 11, 6a and 6b. Similarly, FIG. 3 sets out the wild-type prototype amino acid sequences for the E2 protein of HPV 11, 6a and 6b. It is expected that an immune therapy (therapeutic vaccine) using HPV6b sequences will cross-react to provide a prophylactic or therapeutic immune response against all three viral types.

The codon usage of the HPV6b E1 sequence was compared to that of highly expressed human and *E. coli* genes and found to have a low codon usage coefficient for both species. Simply using the most abundant codon for each amino acid residue would also result in a skewed codon usage pattern, as no organism uses exclusively its most preferred codon for a given amino acid. Consequently, the codons were assigned using a statistical method to give a synthetic gene having a codon frequency closer to that found naturally in highly expressed *E. coli* and human genes.

The codons in the synthetic gene were assigned using a Visual Basic program called Calcgene, written by R. S. Hale and G Thompson (Protein Expression and Purification Vol. 12 pp.185–188 (1998)). For each amino acid residue in the original sequence, a codon was assigned based on the probability of it appearing in highly expressed *E. coli* genes. Details of the program, which works under Microsoft Windows 3.1, can be obtained from the authors. Because the program applies a statistical method to assign codons to the synthetic gene, not all resulting codons are the most frequently used in the target organism. Rather, the proportion of frequently and infrequently used codons of the target organism is reflected in the synthetic sequence by assigning codons in the correct proportions. However, as there is no hard-and-fast rule assigning a particular codon to a particular position in the sequence, each time it is run the program will produce a different synthetic gene—although each will have the same codon usage pattern and each will encode the same amino acid sequence. If the program is run several times for a given amino acid sequence and a given target organism, several different nucleotide sequences will be produced which may differ in the number, type and position of restriction sites, intron splice signals etc., some of which may be undesirable. The skilled artisan will be able to select an appropriate sequence for use in expression of the polypeptide on the basis of these features.

Furthermore, since the codons are randomly assigned on a statistical basis, it is possible (although perhaps unlikely) that two or more codons which are relatively rarely used in the target organism might be clustered in close proximity. It is believed that such clusters may upset the machinery of translation and result in particularly low expression rates, so the algorithm for choosing the codons in the optimized gene excluded any codons with an RSCU value of less than 0.2 for highly expressed genes in order to prevent any rare codon clusters being fortuitously selected. The distribution of the remaining codons was then allocated according to the frequencies for highly expressed *E. coli* genes to give an overall distribution within the synthetic gene that resembled that of the *E. coli* genes (coefficient=0.85) and also that of highly expressed human genes (coefficient=0.5). A similar process was used to obtain a codon optimised nucleotide sequence for HPV E2, except that Syngene (Peter Ertl, unpublished), an updated version of the Calcgene program, allowing exclusion of rare codons to be optional, was used to allocate codons according to the codon frequency pattern of highly expressed human genes. Unlike the codon assignment for E, rare codons were not excluded. At the same time, an alteration was made to one of the oligonucleotides to encode a K A amino acid change, as described below.

Mutations were introduced into the codon optimised E and E2 genes to give rise to point mutations in the E (K83G, R84G and G483D) and E2 (K A) amino acid sequences. The amino acid sequences of the mutated genes are shown (aligned with the wild-type prototype sequence) in FIGS. 2 (HPV6bE) and 4 (HPV6bE2 and HPV E2). The codon optimised and mutated nucleotide sequence for HPV6b E is shown in FIGS. 5*a* and 5*b*. The codon optimised and mutated nucleotide sequence for HPV E2 is shown in FIG. 6. In FIG. 4, the amino acid sequence of the polypeptide obtained by expression of the codon optimised and mutated HPV E2 gene is also given, in alignment with the prototype wild-type and the mutated wild-type sequences, to show that codon optimisation of the nucleotide sequence does not alter the amino acid sequence encoded (which is identical to the mutated wild-type sequence).

EXAMPLE 2

Construction of the Codon Optimised HPV6b E1 Polynucleotide Sequence

Gene Design:

Using the optimisation software discussed above, overlapping 40mer oligonucleotides were calculated from the optimised sequence. The terminal oligonucleotides containing the restriction sites were 60mers. The oligonucleotides were ordered from Life Technologies Ltd at 50 nmole concentration, deprotected and non-phosphorylated.

Oligonucleotide Assembly:

Each oligonucleotide was dissolved in double distilled water to a final concentration of 100 micromolar (µM) and an equal mixture was prepared of all 96 oligonucleotides at 100 µM. The synthesis was set up as follows using Pwo polymerase from Roche Boehringer (Cat No. 1 644 955).

| Double distilled water | 86 µl |
|---|---|
| Pwo 10X buffer | 10 µl |
| dNTP mix | 1 µl (equal mix of 100 mM dNTPs) |
| oligo mix | 1 µl (equal mix of 100 µM oligos) |
| Pwo polymerase | 2 µl. |

A Polymerase Chain Reaction (PCR) was carried out on the above reaction mix on a Trio Thermoblock (Biometra) using the following conditions:

| 1. | 40° C. | 2 min |
|---|---|---|
| 2. | 72° C. | 10 sec |
| 3. | 94° C. | 15 sec |
| 4. | 40° C. | 30 sec |
| 5. | 72° C. | 20 sec + 2 secs per cycle |
| 6. | 4° C. | ∞ |

Cycle repeated 25 times between steps 3 and 5.

After completion of 25 cycles, a 10 µl aliquot was removed from each tube and run on a 0.8% Tris Acetate (TAE) agarose gel and observed under long wave UV light. The expected size of the synthesised E1 DNA should be approx. 2 kb.

Gene Recovery:

The synthetic gene was recovered by PCR using polymerase using the two terminal oligos which contained a Not 1 restriction site on the N terminal of the synthetic oligo and a Bam H1 site at the C terminal synthetic oligo.

| Double distilled water | 65 µl |
|---|---|
| Pwo 10X buffer | 10 µl |
| dNTP mix | 1 µl (equal mix of 100 mM dNTPs) |
| assembly mix | 20 µl (from previous PCR) |
| N terminal oligo | 1 µl (100 µM) |
| C terminal oligo | 1 µl (100 µM) |
| Pwo polymerase | 2 µl. |

| 1. | 94° C. | 45 sec |
|---|---|---|
| 2. | 72° C. | 2 min + 1 min per 500 bp |
| 3. | 72° C. | 10 min |
| 4. | 4° C. | ∞ |

Cycle repeated 25 times between steps 2 and 1.

The PCR product was then purified using a QIAquick PCR purification kit (Qiagen Cat No. 28104) before the DNA was resuspended in a total of 50 µl of kit elution buffer. A 10 µl aliquot was digested with Not 1 and BamH1 restriction enzymes (from Life Technologies Ltd, 3 Fountain Drive, Inchinnan Business Park, Paisley, Scotland) for 2 hours at 37° C. This digest was gel purified on 0.8% TAE agarose gel and the 2 kb DNA product excised and extracted using a QIAquick Gel extraction Kit (Qiagen Cat No. 28704). The final digested pure DNA fragment was eluted in a total of 50 µl of kit elution buffer.

This PCR fragment was cloned into vector p7313PLc (FIG. 7), (Powderject Vaccines Inc., see further details below) and transformed into competent JM109 cells (Promega cat no: P9751). Plasmid DNA from selected clones were restriction enzyme checked by digestion with Nco 1-BamH 1 and Nco 1-EcoR1. Five correct clones with 2 kb fragment inserts were selected and the insert DNA's sequenced. One clone with an insert containing just three point mutations was selected for further use. The three point mutations were corrected by ligation swap with homologous small fragments from other clones.

The corrected clone was re-checked by restriction enzyme digestion and the insert DNA fully sequenced. This cloned was designated p6bE1c/o. At the same time and for comparative expression and immunisation studies the wild type HPV-6b E1 gene, and the wild type HPV-11 E1 gene were PCR amplified from genomic clones of HPV-6b, (EMBO J. 2 (12) 2314–2318 1983) and HPV-11 (Virology 151, 124–130 1986), and the respective fragments cloned into Not 1-BamH1 digested vector p7313PLc. These clones were designated p6bE:1w/t and p11E1w/t respectively.

The E1 genes in clones p6bE1c/o and p6bE1w/t were further mutated to introduce amino acid changes K83G, R84G and G438D. Sequenced matched 3' and 5' oligonucleotide primers with nucleotide substitutions designed to introduce the required mutations were used in PCR reactions with other kit reagents by methods described in Quick-Change Site-Directed Mutagenesis Kit (Stratagene Cat No. 200518). Mutated p6bE1c/o and p6bE1w/t clones were designated p6bE1c/o mut and, p6bE1 w/t mut respectively.

EXAMPLE 3

Construction of the Codon Optimised HPV11 E2 Polynucleotide Sequence

The design, assembly and recovery of the E2 codon optimised gene was as described above for E1, but the overlapping oligonucleotides were 60 nucleotides in length rather than 40, with an 18 nt overlap. Unlike in the E1 procedure a clone containing the K111 A amino acid mutation was generated at the same time as the codon optimised E2 gene clone by substituting the two appropriate wild type sequence oligonucleotides with two 60mer oligonucleotides which together comprise the nucleotide substitution required to generate the K111A change.

Composition of Plasmid p7313-PLc

The plasmid was constructed by replacing the beta-lactamase gene containing Eam 11051-Pst1 fragment of pUC19 (available from Amersham Pharmacia Biotech UK Ltd., Amersham Place, Little Chalfont, Bucks, HP7 9NA) with an EcoRI fragment of pUC4K (Amersham-Pharmacia) containing the Kanamycin resistance gene, following blunt ending of both fragments using T4 DNA polymerase. The human Cytomegalovirus IE1 promoter/enhancer, Intron A, was derived from plasmid JW4303 obtained from Dr Harriet Robinson, University of Massachusetts, and inserted into the Sal1 site of pUC19 as a XhoI-Sal1 fragment, incorporating the bovine growth hormone polyadenylation signal. Deletion of the 5' SalI-BanI fragment from the promoter generated the minimal promoter used in the vector (WO00/23592-Powderject Vaccines Inc.). HBV Surface antigen 3'UTR was derived from *Hepatitis B* Virus, serotype adw, in the vector pAM6 (Moriarty et al., Proc. Natl. Acad. Sci. USA, 78, 2606–2610, 1981). pAM6 (pBR322 based vector) was obtained from the American Type Culture Collection, catalogue number ATCC 45020. The 3'UTR was inserted 5' to the polyadenylation signal as a 1.4 kb BamHI fragment, blunt ended for insertion to remove the BamHI sites. In a series of steps (including digestion with Bgl II, Klenow polymerase treatment, digestion with BstX I, digestion with Nco I, treatment with mung bean nuclease to remove overhang and further digestion with BstX I), modifications were made to the region between the 3'untranslated enhancer region of the HBV S gene and bGHpA signal to remove all open reading frames of greater than 5 codons between the X gene promoter and the bGHpA signal. This resulted in deletion of sequence encoding the translatable portion of the X protein (9 amino acids) and the X gene start codon. However, the weak enhancer/promoter region of the X gene was retained because this region was found to enhance expression of HBsAg from the CMV promoter. The bovine growth hormone polyadenylation signal was substituted with the rabbit beta globin polyadenylation signal. The 5' non-coding and coding sequences of the S antigen were excised and replaced with an oligonucleotide linker to provide multiple cloning sites as shown to produce plasmid p7313-PL.

well. 200 µl of OPTI-mem™ was added to each transfection mix, mixed and added gently to a cell monolayer. The plate was incubated for 5 hours at 37° C. in 5% $CO_2$ after which the transfection mix and OPTI-mem™ were discarded. The cell monolayers were washed gently with cell growth medium twice and finally transfected cells were incubated for 24 hours in Dulbecco's Modified Eagle Medium containing 10% foetal calf serum and 29.2 mg/ml of L-glutamine at 37° C. in 5% $CO_2$. The cells were scraped off into microtubes, washed twice with PBS, spun down and the cell pellet was resuspended in SDS Page Laemmli dye. The cell pellets were boiled and loaded onto a 10% SDS Page gel and electrophoresed in 1×Tris Glycine SDS buffer. After electrophoresis, the gel was blotted onto Nitrocellulose membrane (Amersham) and Western Blotted. The nitrocellulose membrane was blocked with 5% Marvel™ (Premier Beverages, Knighton, Adbaston, Stafford, UK) in PBS for 30 min at room temperature and washed twice with PBS and 0.1% Tween 20. A polyclonal antibody raised against the C terminal protein sequence of HPV6bE1 protein sequence: CSSSLDIQDSEDEEDGSNSQAFR [SEQ ID NO. 18] in rabbits, was diluted in 5% Marvel™ in PBS and added to the nitrocellulose membrane. This was incubated at room temperature for 1 hour with gentle agitation. The diluted antibody was removed and the membrane washed three times with PBS and 0.1% Tween 20. A secondary conjugate, Swine anti-rabbit horseradish peroxidase (HRP) (DAKO), was diluted 1:20000 in PBS and 0.1% Tween 20. This was added to the washed membrane and incubated with gentle agitation at room temperature for 1 hour. The membrane was

```
Hind -- - Not I - -- -EcoRV --NdeI-- --BamHI
AGCTTGCGGCCGCTAGCGATATCGGTACCATATGTCGACGGATCC...   [SEQ. ID NO. 16]

...ACGCCGGCGATCGCTATAGCCATGGTCTACAGCTGCCTAGGCCGG   [SEQ. ID NO. 17]
         --NheI--    --KpnI--  -- SalI --  ΔNotI
```

The ColE1 cer sequence was obtained from a subclone from plasmid pDAH212 from David Hodgeson (Warwick University) and amplified by PCR using primers to place EcoRI restriction sites at the ends of the sequence. The cer sequence was then inserted into the EcoRI site of p7313-PL to produce plasmid p7313-PLc (FIG. 7). The sequence of the amplified cer was verified against the Genbank entry M11411.

EXAMPLE 4

Expression of E1 in Mammalian 293T Cells

Mammalian 293T cells were grown at log phase at a final concentration of $2 \times 10^5$ cells per 6 well Corning Costar™ (Corning Science Products, 10 The ValleyCentre, Gordon Road, High Wycombe, Bucks, UK) tissue culture plate overnight at 37° C. in 5% $CO_2$. The following transfection mix was prepared and complexed for 25 minutes:

2 µg of plasmid DNA (vector, p6bE1c/o, p6bE1w/t) in 16 µl sterile double distilled water plus:

| | |
|---|---|
| OPTI-mem ™ (Gibco BRL, Paisley, Scotland) | 8 µl |
| Lipofectamine ™ (GibcoBRL) | 6 µl. |

Each cell monolayer was washed carefully twice with OPTI-mem™. 800 µl of OPTI-mem™ was added to each then washed thoroughly with PBS and 0.1% Tween20. A Chemiluminescent HRP kit (Amersham) was used to detect the transferred proteins on the membrane.

Results:

The predicted size of a translated protein for E1 is 68 kDa–72 kDa. The results (FIG. 8) show a correct protein size expressed by p7313-PLc containing the codon optimised HPV6bE1 (lane 4). Vector containing wild-type E1 is in lane 3, which shows that there was no detectable expression of E1 in human cells from the wild-type nucleotide sequence. Similarly no E1 is detected in lane 2 (empty vector) and lane 1 (untransfected cells). The approx. 60 kD band in lanes 1–4 is an unidentified cellular protein which cross-reacts with the anti-E1 antibody. The band is of roughly constant intensity across the lanes, showing that the loading of the samples was consistent.

EXAMPLE 5

Construction of Recombinant Vaccinia Virus Expressing HPV E1 and HPV E2 Proteins.

Vaccinia virus expressing HPV-6b E1 protein was generated at Glaxo Wellcome, Stevenage, UK. Vaccinia virus expressing HPV-11 E1 and HPV-11 E2 were a kind gift from Jeff Engler, University of Alabama at Birmingham, US.

Briefly, the E1 gene from p6bE1w/t was cloned into Vaccinia virus vector pTM3 and then the restriction enzyme checked and DNA sequenced recombinant vector used to transfected HTk⁻cells. Recombinant Vaccinia virus was isolated and plaque purified. E1 protein expression was checked by Western blotting using peptide antisera after infection of permissive cells with both the recombinant virus expressing HPV-6b E1 and, a second Vaccinia virus (vTF7-3) expressing bacteriophage T7 RNA polymerase. Co-infection of cells with Vaccinia virus vFT7-3 is also necessary in order to direct expression of E1 and E2 protein from the HPV-11 E1 and E2 recombinant Vaccinia viruses. Vaccinia virus strain WR was used in negative control experiments. Vector pTM3 and virus vTF7-3 were from National Institute of Health, Maryland, US.

EXAMPLE 6

Immunology—Detection of Cellular Responses to HPV Antigens

All reagents were obtained from Gibco BRL, Paisley, Scotland or Sigma, Poole, Dorset unless otherwise stated.

A. Immunisation Protocol.

Female C57BL/6 mice were immunised with 1.0–2.0 μg DNA (either p6bE1c/o, p6bE1w/t, p6bE1c/o mut, p6bE1w/t mut or empty plasmid p7313PLc) by PMDD and boosted with an identical dose 14 days later. Animals were sacrificed by cervical dislocation and spleens removed for investigation of the cellular responses to HPV antigens.

B. Preparation of Single Cell Suspension of Splenocytes.

Spleens were "mashed" between ground glass slides (BDH), red blood cells lysed (155 mM $NH_4Cl$, 10 mM $KHCO_3$, 0.1 mM EDTA) and cells resuspended in complete RPMI. (RPMI-1640 medium supplemented with 10% foetal calf serum (FCS), 2 mM glutamine, 100 units/ml penicillin, 100 μg/ml *streptomycin* and $5 \times 10^{-5}$ M 2-mercaptoethanol).

C. Infection of MC57 Target Cells.

Immunodominant epitopes derived from HPV antigens remain undefined therefore the detection of antigen specific responses in vitro relies on natural processing of whole antigen generated within target cells that have been transfected with cDNA encoding the whole protein(s). MC57 cells ($K^b$ positive) were infected with recombinant vaccinia virus expressing HPV-6b E1, HPV-11 E2 or HPV-11 E1 using a multiplicity of infection of 5 for 1 hour at 37° C. Excess virus was washed off and cells resuspended in complete RPMI containing 50 ng/ml recombinant human IL-2 (Glaxo Wellcome, Geneva).

D. ELISPOT.

ELISPOT plates (96 well, Millipore MAIP S 45 1 0) were coated with rat anti-mouse IFN gamma (Pharmingen 18181 D) at 15 μg/ml in PBS overnight (4° C.) prior to the addition of 4×10e5 splenocytes obtained from experimental groups. Antigen was presented by the addition of 1×10e4 recombinant vaccinia infected MC57 cells. Wild-type vaccinia strain WR was used as a negative control. The assay was incubated overnight at 37° C. (5% $CO_2$).

On day 2 of the assay, spot forming cells were detected using biotinylated rat anti-mouse IFN gamma (Pharmingen 18112D) at 1 μg/ml followed by streptavidin alkaline phosphatase conjugate (TCS biologicals SA 1008) at 1/1000 dilution in PBS. This was visualised using an alkaline phosphatase substrate kit (Biorad 170–6432) and quantified by image analysis. The results are shown in FIG. 9.

Figure 9:
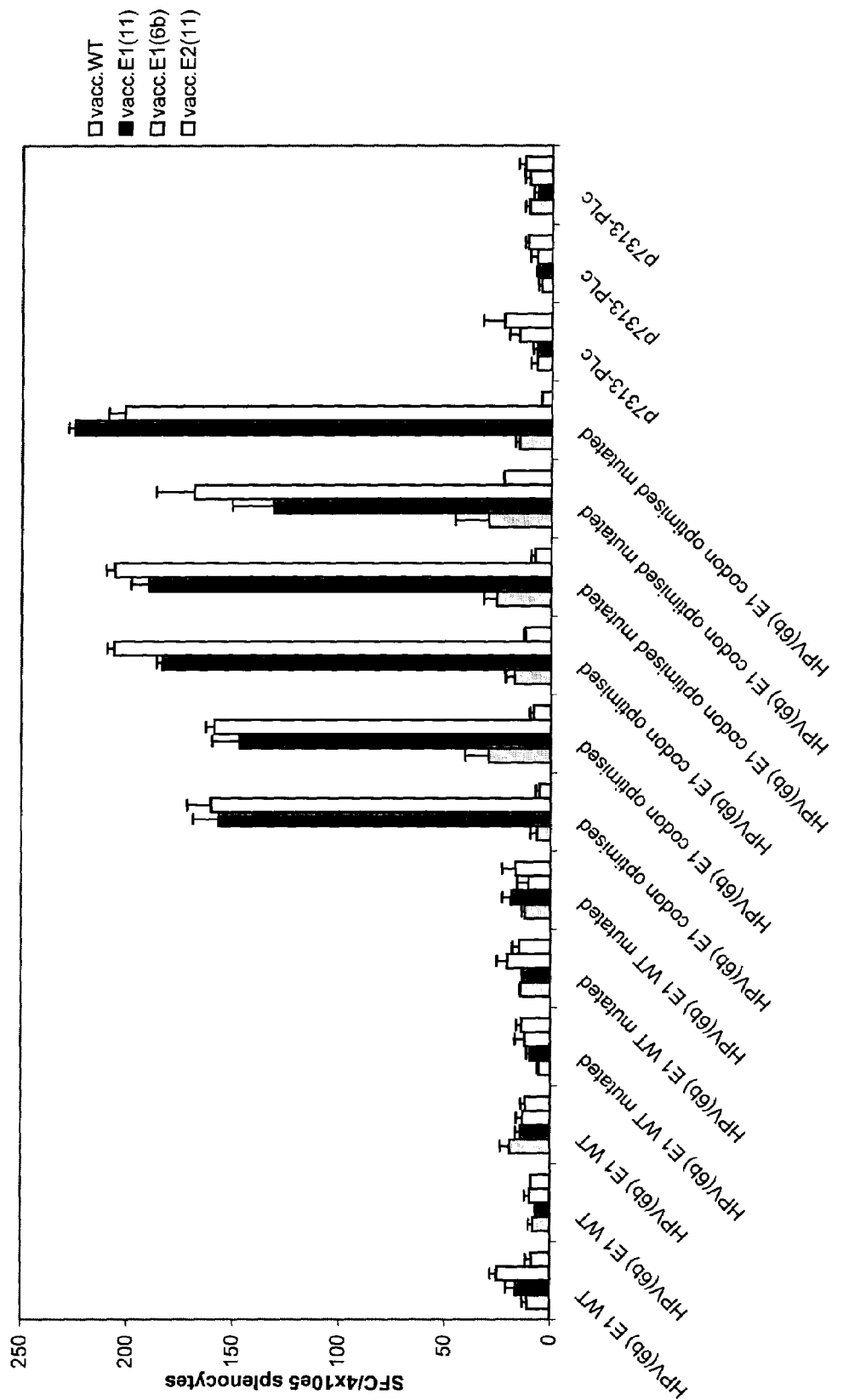
FIG. 9 shows cellular responses to antigen challenge after immunisation of mice with a polynucleotide according to the invention (Example 6)

As can be seen from FIG. 9, a strong cellular response was seen from all three mice vaccinated with plasmid encoding HPV-6b codon optimised E1 sequence, when challenged with E1 carried in the vaccinia vector (vacc.E1(11) or vacc.E1(6b)). No response was seen when these mice were challenged with wild-type vaccinia (vacc.WT), or with vaccinia expressing HPV-11 E2 (vacc.E2(11)). By contrast, vaccination of mice with plasmid encoding the wild type E1 sequence does not result in a T-cell response. Splenocytes from these mice do not react to challenge by vaccinia carrying the E1 gene, nor to any other challenge (data not shown). Mutation of the E1 gene does not alter the cellular response in mice. Also, since mice immunised with p6bE1 c/o and p6bE1 c/o mut raised strong cellular immune responses against target cells infected with a Vaccinia virus expressing E1 protein from HPV-11, we can assume that there is a high level of immunlogic cross reactivity between HPV-6b E1 and HPV-11 E1. Mice vaccinated with empty p7313-PLc vector showed no response to any challenge.

EXAMPLE 7

Figure 10:
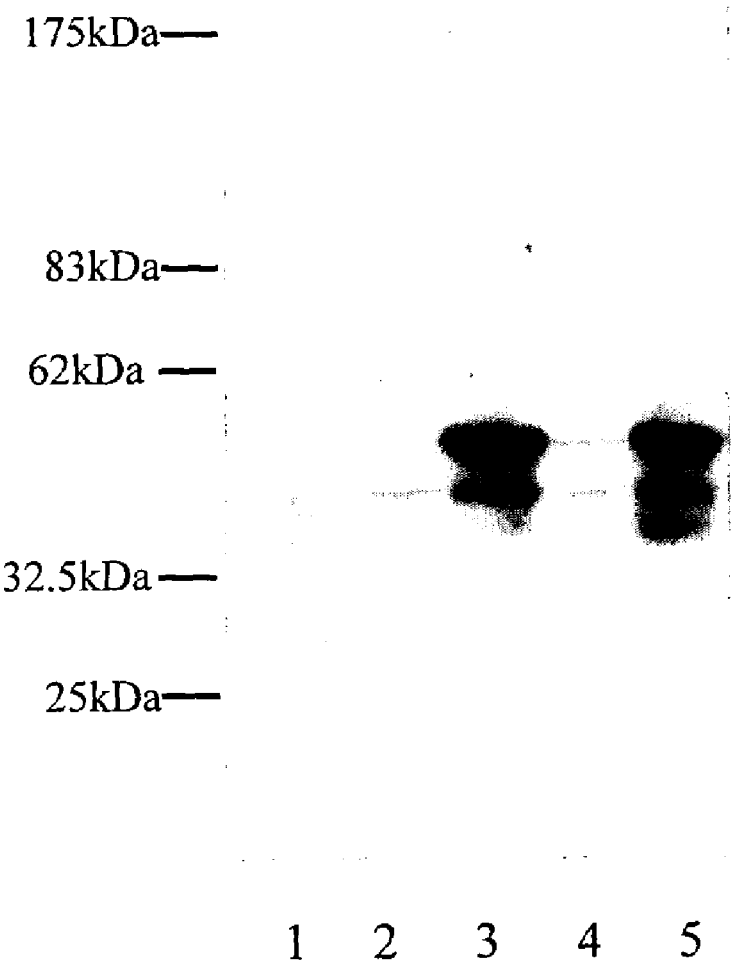
FIG. 10 shows cell lysate samples from Example 7 run on an acrylamide gel and stained to show antibody binding to expressed E2 protein.

Expression of HPV 6b E2 in Mammalian 293T Cells 293T cell monolayers (80% confluent) in 24 well plates were transfected with 1 μg of each plasmid (p6bw/t, p6bc/o, p6bw/t mut, p6bc/o mut) using 2.5 μl of Lipofectamine 2000 (Life Technologies) per transfection following the standard protocol (see Example 4 above). 24 hrs after transfection the cells were harvested, rinsed in phosphate buffered saline and examined by SDS-PAGE and Western blot using an anti-E2 peptide antiserum (#1100) raised against HPV-6b N-terminal amino acid sequence MEAIAKRLDACQEQLLELY-EEC [SEQ. ID NO. 19] (FIG. 10).

Results

The results show a major protein band of the expected size (40 kd–45 kD) in track 3 (codon optimised E2) and track 5 (codon optimised and mutated E2). A minor band of the same size also appears in track 4 indicating some very low level expression from the mutated wild type E2 plasmid, but not in track 1 (negative control), or in track 2 (wild type E2 protein). A cross reacting protein band of ~25 kd appears in all tracks indicating equal loading of protein lysates. Mutation of E2 does not appear to compromise E2 protein expression which is significant improved by codon-optimisation.

EXAMPLE 8

Example: PMID delivery of codon-optimised COPV E1 plasmid protects from mucosal challenge with Canine Oral Papillomavirus in dogs Introduction The canine oral papillomavirus (COPV) animal model is a good mimic of mucosal human papillomavirus disease. The features of disease caused in dogs by COPV are very similar to that which occurs in humans (Nicholls et al Virology 2001, 283(1) 31–39). Importantly it is a mucosal papillomavirus disease model. The COPV virus infects the canine mucosal epithelia and, after a lag period of a few weeks warts appear which then regress spontaneously after an additional period of some weeks. The COPV virus encodes homologues of each of the human papillomavirus genes (E1, E2, E4, E6, E7, L1 and L2).

The dog COPV mucosal disease model has previously been used as a key model in developing the rationale for human virus-like-particle (VLP) papillomavirus vaccines (Ghim et al, Vaccines 1995 25, 375–379, Suzich et al, PNAS 1995, 92 11553–11557). Human papillomavirus VLP vaccines are now in development, and early stage clinical trials have recently been completed in humans.

We show that plasmid DNA encoding a codon-otimised COPV E1 gene when administered by PMID fully protects against virus challenge in the COPV disease model. This is in contrast to plasmid encoding the wild type COPV E1 gene which is not protective.

Methods

Construction of the Wild Type COPV E1 Vector

The gene encoding the COPV E1 wild type sequence was derived from pBR322.COPV. Plasmid pBR322.COPV contains the entire COPV genome and was a gift from DFKZ Referenzzentrum Fur Humanpathologie Papillomviren, Heidelberg, Germany.

The wild type COPV E1 gene sequence was recovered by PCR and cloned into vector WRG7 77 (Powderject Vaccines Inc). This clone was designated pCOPVE1 w/t.

Construction of the Codon-Optimised COPV E1 Vector

A synthetic gene encoding a codon-optimised COPV E1 gene was generated using methods described in Example 1. The synthetic gene was cloned into vector WRG7 77. This clone was designated pCOPVE1 c/o.

Construction of COPV E1 Baculovirus

The E1 gene was recovered by PCR from pBR322.COPV and cloned into vector pFastBacHtb (Gibco). A recombinant baculovirus clone designated pFastBacCOPVE1 was generated as described above. Lysates of pFastBacCOPVE1 were prepared as described above.

Construction of the Wild Type COPV L1 Vector

The major capsid gene L1 gene was derived from pBR322.COPV by PCR and cloned into vector WRG7077. This clone was designated pCOPVL1 w/t.

Antisera to COPV E1

Rabbit anti-peptide polyclonal antibodies were used to detect COPV E1 protein expression by western blotting. Antisera were generated from rabbits immunised with N terminal, and a C-terminal peptide protein sequence from COPV E1.

N-terminal COPV E1 peptide:

```
MAARKGTDSETEDGGC        [SEQ. ID NO. 20]
```

C-terminal COPV E1 peptide:

```
CKHLDLSDPEDGEDGETQRG    [SEQ. ID NO 21]
```

Results

Expression of COPV E1 in Mamalian Cells

A pFastBacCOPVE1 infected insect cell lysate, and a lysate from pCOPVE1w/t and pCOPVE1 c/o transfected 293T cells were electrophoresed, blotted and then probed using COPV E1 anti-peptide antisera as described in above.

Proteins of the expected size appear in track A (baculovirus lysate) (FIG. 11) and track D (pCOPVE1 c/o) only. The COPV E1 protein expressed in baculovirus is histidine tagged and so is slightly larger than the protein expressed in mammalina cells (compare tracks A and C). There is no detectable expression of COPV E1 protein in cells transfected with pCOPV E1w/t (lane C). Similarly no E1 is detected in lane B (empty vector). A band of ~55 kD band appears in lanes B, C and D. This is an unidentified cross-reacting cellular protein. Both this band and other cross-reacting bands can be seen and these are of roughly constant intensity across the lanes, showing that the loading of the samples was consistent.

Codon-optimisation significantly improves expression of COPV E 1 in mammalian cells, extending and supporting our previous findings for the human E1 gene (FIG. 11).

Immunisation of Beagle Dogs with pCOPVE1 w/t pCOPVE1 c/o and pCOPV L1 Using PMID Female Beagle dogs were immunised by PMID with each of three purified plasmids pCOPVE1 w/t, pCOPVE1 c/o, and pCOPVL1. All vaccinations were performed under general anesthesia. There were five animals in both E1 groups and four animals in the L1 group. Six weeks after the first vaccination, boosting vaccination was undertaken in an identical manner, using the same procedure.

Immunised animals were challenged with infectious COPV virus 2 weeks after the final boosting immunisation. The mucosa of the upper lip of each animal was lightly scarified. 1 μl of purified COPV virus preparation was applied to each of ten sites (five on each side of the upper lip) and allowed to absorb for a few minutes. The isolation and purification of infectious COPV virus has been described (Virology 1999, 265 (2) 365–374).

After challenge with COPV virus the sites of mucosal challenge were examined weekly. The time (after challenge) of wart (papilloma) appearance, and wart size (mm) was measured. None of the animals vaccinated with COPV L1 developed papillomas at any of the challenge sites, supporting previous observations (Vaccine 2 1 19, 2783–2792).

In animals immunised with pCOPVE1 w/t plasmid papillomas had appeared by week five after challenge. Papilloma's grew in size, peaking in size at week 8 before slowly regressing over the next 6 weeks. In contrast, animals immunised with pCOPVE 1 c/o were completely protected from disease (FIG. 12).

Plasmid DNA encoding a codon-otimised COPV E1 gene when administered by PMID fully protects against virus challenge in the COPV disease model. This is in contrast to plasmid encoding the wild type COPV E1 gene which is not protective. See FIG. 12.

SEQUENCE LISTING

```
<160> NUMBER OF SEQ ID NOS: 21

<210> SEQ ID NO 1
<211> LENGTH: 649
<212> TYPE: PRT
<213> ORGANISM: Human papillomavirus type 6a
```

<400> SEQUENCE: 1

```
Met Ala Asp Asp Ser Gly Thr Glu Asn Glu Gly Ser Gly Cys Thr Gly
  1               5                  10                  15

Trp Phe Met Val Glu Ala Ile Val Gln His Pro Thr Gly Thr Gln Ile
             20                  25                  30

Ser Asp Asp Glu Asp Glu Val Glu Asp Ser Gly Tyr Asp Met Val
         35                  40                  45

Asp Phe Ile Asp Asp Ser Asn Ile Thr His Asn Ser Leu Glu Ala Gln
         50                  55                  60

Ala Leu Phe Asn Arg Gln Glu Ala Asp Thr His Tyr Ala Thr Val Gln
 65                  70                  75                  80

Asp Leu Lys Arg Lys Tyr Leu Gly Ser Pro Tyr Val Ser Pro Ile Asn
             85                  90                  95

Thr Ile Ala Glu Ala Val Glu Ser Glu Ile Ser Pro Arg Leu Asp Ala
                100                 105                 110

Ile Lys Leu Thr Arg Gln Pro Lys Lys Val Lys Arg Arg Leu Phe Gln
             115                 120                 125

Thr Arg Glu Leu Thr Asp Ser Gly Tyr Gly Tyr Ser Glu Val Glu Ala
 130                 135                 140

Gly Thr Gly Thr Gln Val Glu Lys His Gly Val Pro Glu Asn Gly Gly
 145                 150                 155                 160

Asp Gly Gln Glu Lys Asp Thr Gly Arg Asp Ile Glu Gly Glu His
                 165                 170                 175

Thr Glu Ala Glu Ala Pro Thr Asn Ser Val Arg Glu His Ala Gly Thr
                 180                 185                 190

Ala Gly Ile Leu Glu Leu Leu Lys Cys Lys Asp Leu Arg Ala Ala Leu
             195                 200                 205

Leu Gly Lys Phe Lys Glu Cys Phe Gly Leu Ser Phe Ile Asp Leu Ile
 210                 215                 220

Arg Pro Phe Lys Ser Asp Lys Thr Thr Cys Leu Asp Trp Val Val Ala
 225                 230                 235                 240

Gly Phe Gly Ile His His Ser Ile Ser Glu Ala Phe Gln Lys Leu Ile
                 245                 250                 255

Glu Pro Leu Ser Leu Tyr Ala His Ile Gln Trp Leu Thr Asn Ala Trp
                 260                 265                 270

Gly Met Val Leu Leu Val Leu Leu Arg Phe Lys Val Asn Lys Ser Arg
             275                 280                 285

Ser Thr Val Ala Arg Thr Leu Ala Thr Leu Asn Ile Pro Glu Asn
             290                 295                 300

Gln Met Leu Ile Glu Pro Pro Lys Ile Gln Ser Gly Val Ala Ala Leu
 305                 310                 315                 320

Tyr Trp Phe Arg Thr Gly Ile Ser Asn Ala Ser Thr Val Ile Gly Glu
                 325                 330                 335

Ala Pro Glu Trp Ile Thr Arg Gln Thr Val Ile Glu His Gly Leu Ala
             340                 345                 350

Asp Ser Gln Phe Lys Leu Thr Glu Met Val Gln Trp Ala Tyr Asp Asn
             355                 360                 365

Asp Ile Cys Glu Glu Ser Glu Ile Ala Phe Glu Tyr Ala Gln Arg Gly
             370                 375                 380

Asp Phe Asp Ser Asn Ala Arg Ala Phe Leu Asn Ser Asn Met Gln Ala
 385                 390                 395                 400

Lys Tyr Val Lys Asp Cys Ala Thr Met Cys Arg His Tyr Lys His Ala
                 405                 410                 415
```

```
Glu Met Arg Lys Met Ser Ile Lys Gln Trp Ile Lys His Arg Gly Ser
            420                 425                 430

Lys Ile Glu Gly Thr Gly Asn Trp Lys Pro Ile Val Gln Phe Leu Arg
            435                 440                 445

His Gln Asn Ile Glu Phe Ile Pro Phe Leu Thr Lys Phe Lys Leu Trp
            450                 455                 460

Leu His Gly Thr Pro Lys Lys Asn Cys Ile Ala Ile Val Gly Pro Pro
465                 470                 475                 480

Asp Thr Gly Lys Ser Tyr Phe Cys Met Ser Leu Ile Ser Phe Leu Gly
            485                 490                 495

Gly Thr Val Ile Ser His Val Asn Ser Ser His Phe Trp Leu Gln
            500                 505                 510

Pro Leu Val Asp Ala Lys Val Ala Leu Leu Asp Asp Ala Thr Gln Pro
            515                 520                 525

Cys Trp Ile Tyr Met Asp Thr Tyr Met Arg Asn Leu Leu Asp Gly Asn
            530                 535                 540

Pro Met Ser Ile Asp Arg Lys His Lys Ala Leu Thr Leu Ile Lys Cys
545                 550                 555                 560

Pro Pro Leu Leu Val Thr Ser Asn Ile Asp Ile Thr Lys Glu Asp Lys
            565                 570                 575

Tyr Lys Tyr Leu His Thr Arg Val Thr Thr Phe Thr Phe Pro Asn Pro
            580                 585                 590

Phe Pro Phe Asp Arg Asn Gly Asn Ala Val Tyr Glu Leu Ser Asn Thr
            595                 600                 605

Asn Trp Lys Cys Phe Phe Glu Arg Leu Ser Ser Ser Leu Asp Ile Gln
            610                 615                 620

Asp Ser Glu Asp Glu Asp Gly Ser Asn Ser Gln Ala Phe Arg Cys
625                 630                 635                 640

Val Pro Gly Thr Val Val Arg Thr Leu
            645
```

<210> SEQ ID NO 2
<211> LENGTH: 649
<212> TYPE: PRT
<213> ORGANISM: Human papillomavirus type 6a

<400> SEQUENCE: 2

```
Met Ala Asp Asp Ser Gly Thr Glu Asn Glu Gly Ser Gly Cys Thr Gly
1               5                   10                  15

Trp Phe Met Val Glu Ala Ile Val Gln His Pro Thr Gly Thr Gln Ile
            20                  25                  30

Ser Asp Asp Glu Asp Glu Glu Val Glu Asp Ser Gly Tyr Asp Met Val
            35                  40                  45

Asp Phe Ile Asp Asp Ser Asn Ile Thr His Asn Ser Leu Glu Ala Gln
50                  55                  60

Ala Leu Phe Asn Arg Gln Glu Ala Asp Thr His Tyr Ala Thr Val Gln
65                  70                  75                  80

Asp Leu Lys Arg Lys Tyr Leu Gly Ser Pro Tyr Val Ser Pro Ile Asn
            85                  90                  95

Thr Ile Ala Glu Ala Val Glu Ser Glu Ile Ser Pro Arg Leu Asp Ala
            100                 105                 110

Ile Lys Leu Thr Arg Gln Pro Lys Lys Val Lys Arg Arg Leu Phe Gln
            115                 120                 125

Thr Arg Glu Leu Thr Asp Ser Gly Tyr Gly Tyr Ser Glu Val Glu Ala
            130                 135                 140
```

-continued

```
Gly Thr Gly Thr Gln Val Glu Lys His Gly Val Pro Glu Asn Gly Gly
145                 150                 155                 160

Asp Gly Gln Glu Lys Asp Thr Gly Arg Asp Ile Glu Gly Glu Glu His
                165                 170                 175

Thr Glu Ala Glu Ala Pro Thr Asn Ser Val Arg Glu His Ala Gly Thr
            180                 185                 190

Ala Gly Ile Leu Glu Leu Leu Lys Cys Lys Asp Leu Arg Ala Ala Leu
        195                 200                 205

Leu Gly Lys Phe Lys Glu Cys Phe Gly Leu Ser Phe Ile Asp Leu Ile
    210                 215                 220

Arg Pro Phe Lys Ser Asp Lys Thr Thr Cys Ala Asp Trp Val Val Ala
225                 230                 235                 240

Gly Phe Gly Ile His His Ser Ile Ser Glu Ala Phe Gln Lys Leu Ile
                245                 250                 255

Glu Pro Leu Ser Leu Tyr Ala His Ile Gln Trp Leu Thr Asn Ala Trp
                260                 265                 270

Gly Met Val Leu Leu Val Leu Val Arg Phe Lys Val Asn Lys Ser Arg
            275                 280                 285

Ser Thr Val Ala Arg Thr Leu Ala Thr Leu Leu Asn Ile Pro Asp Asn
        290                 295                 300

Gln Met Leu Ile Glu Pro Pro Lys Ile Gln Ser Gly Val Ala Ala Leu
305                 310                 315                 320

Tyr Trp Phe Arg Thr Gly Ile Ser Asn Ala Ser Thr Val Ile Gly Glu
                325                 330                 335

Ala Pro Glu Trp Ile Thr Arg Gln Thr Val Ile Glu His Gly Leu Ala
                340                 345                 350

Asp Ser Gln Phe Lys Leu Thr Glu Met Val Gln Trp Ala Tyr Asp Asn
            355                 360                 365

Asp Ile Cys Glu Glu Ser Glu Ile Ala Phe Glu Tyr Ala Gln Arg Gly
        370                 375                 380

Asp Phe Asp Ser Asn Ala Arg Ala Phe Leu Asn Ser Asn Met Gln Ala
385                 390                 395                 400

Lys Tyr Val Lys Asp Cys Ala Thr Met Cys Arg His Tyr Lys His Ala
                405                 410                 415

Glu Met Arg Lys Met Ser Ile Lys Gln Trp Ile Lys His Arg Gly Ser
                420                 425                 430

Lys Ile Glu Gly Thr Gly Asn Trp Lys Pro Ile Val Gln Phe Leu Arg
            435                 440                 445

His Gln Asn Ile Glu Phe Ile Pro Phe Leu Ser Lys Phe Lys Leu Trp
450                 455                 460

Leu His Gly Thr Pro Lys Lys Asn Cys Ile Ala Ile Val Gly Pro Pro
465                 470                 475                 480

Asp Thr Gly Lys Ser Tyr Phe Cys Met Ser Leu Ile Ser Phe Leu Gly
                485                 490                 495

Gly Thr Val Ile Ser His Val Asn Ser Ser Ser His Phe Trp Leu Gln
            500                 505                 510

Pro Leu Val Asp Ala Lys Val Ala Leu Leu Asp Asp Ala Thr Gln Pro
        515                 520                 525

Cys Trp Ile Tyr Met Asp Thr Tyr Met Arg Asn Leu Leu Asp Gly Asn
    530                 535                 540

Pro Met Ser Ile Asp Arg Lys His Lys Ala Leu Thr Leu Ile Lys Cys
545                 550                 555                 560
```

```
                    -continued

Pro Pro Leu Leu Val Thr Ser Asn Ile Asp Ile Thr Lys Glu Glu Lys
            565                 570                 575

Tyr Lys Tyr Leu His Thr Arg Val Thr Thr Phe Thr Phe Pro Asn Pro
            580                 585                 590

Phe Pro Phe Asp Arg Asn Gly Asn Ala Val Tyr Glu Leu Ser Asn Ala
            595                 600                 605

Asn Trp Lys Cys Phe Phe Glu Arg Leu Ser Ser Ser Leu Asp Ile Gln
            610                 615                 620

Asp Ser Glu Asp Glu Glu Asp Gly Ser Asn Ser Gln Ala Phe Arg Cys
625                 630                 635                 640

Val Pro Gly Thr Val Val Arg Thr Leu
            645

<210> SEQ ID NO 3
<211> LENGTH: 649
<212> TYPE: PRT
<213> ORGANISM: Human papillomavirus type 11

<400> SEQUENCE: 3

Met Ala Asp Asp Ser Gly Thr Glu Asn Glu Gly Ser Gly Cys Thr Gly
  1               5                  10                  15

Trp Phe Met Val Glu Ala Ile Val Glu His Thr Thr Gly Thr Gln Ile
                 20                  25                  30

Ser Glu Asp Glu Glu Glu Val Glu Asp Ser Gly Tyr Asp Met Val
             35                  40                  45

Asp Phe Ile Asp Asp Arg His Ile Thr Gln Asn Ser Val Glu Ala Gln
 50                  55                  60

Ala Leu Phe Asn Arg Gln Glu Ala Asp Ala His Tyr Ala Thr Val Gln
65                  70                  75                  80

Asp Leu Lys Arg Lys Tyr Leu Gly Ser Pro Tyr Val Ser Pro Ile Ser
                85                  90                  95

Asn Val Ala Asn Ala Val Glu Ser Glu Ile Ser Pro Arg Leu Asp Ala
                100                 105                 110

Ile Lys Leu Thr Thr Gln Pro Lys Lys Val Lys Arg Arg Leu Phe Glu
            115                 120                 125

Thr Arg Glu Leu Thr Asp Ser Gly Tyr Gly Tyr Ser Glu Val Glu Ala
            130                 135                 140

Ala Thr Gln Val Glu Lys His Gly Asp Pro Glu Asn Gly Gly Asp Gly
145                 150                 155                 160

Gln Glu Arg Asp Thr Gly Arg Asp Ile Glu Gly Glu Gly Val Glu His
                165                 170                 175

Arg Glu Ala Glu Ala Val Asp Asp Ser Thr Arg Glu His Ala Asp Thr
                180                 185                 190

Ser Gly Ile Leu Glu Leu Leu Lys Cys Lys Asp Ile Arg Ser Thr Leu
            195                 200                 205

His Gly Lys Phe Lys Asp Cys Phe Gly Leu Ser Phe Val Asp Leu Ile
            210                 215                 220

Arg Pro Phe Lys Ser Asp Arg Thr Thr Cys Ala Asp Trp Val Val Ala
225                 230                 235                 240

Gly Phe Gly Ile His His Ser Ile Ala Asp Ala Phe Gln Lys Leu Ile
                245                 250                 255

Glu Pro Leu Ser Leu Tyr Ala His Ile Gln Trp Leu Thr Asn Ala Trp
            260                 265                 270

Gly Met Val Leu Leu Val Leu Ile Arg Phe Lys Val Asn Lys Ser Arg
            275                 280                 285
```

```
Cys Thr Val Ala Arg Thr Leu Gly Thr Leu Leu Asn Ile Pro Glu Asn
    290                 295                 300
His Met Leu Ile Glu Pro Pro Lys Ile Gln Ser Gly Val Arg Ala Leu
305                 310                 315                 320
Tyr Trp Phe Arg Thr Gly Ile Ser Asn Ala Ser Thr Val Ile Gly Glu
                325                 330                 335
Ala Pro Glu Trp Ile Thr Arg Gln Thr Val Ile Glu His Ser Leu Ala
                340                 345                 350
Asp Ser Gln Phe Lys Leu Thr Glu Met Val Gln Trp Ala Tyr Asp Asn
                355                 360                 365
Asp Ile Cys Glu Glu Ser Glu Ile Ala Phe Glu Tyr Ala Gln Arg Gly
    370                 375                 380
Asp Phe Asp Ser Asn Ala Arg Ala Phe Leu Asn Ser Asn Met Gln Ala
385                 390                 395                 400
Lys Tyr Val Lys Asp Cys Ala Ile Met Cys Arg His Tyr Lys His Ala
                405                 410                 415
Glu Met Lys Lys Met Ser Ile Lys Gln Trp Ile Lys Tyr Arg Gly Thr
                420                 425                 430
Lys Val Asp Ser Val Gly Asn Trp Lys Pro Ile Val Gln Phe Leu Arg
            435                 440                 445
His Gln Asn Ile Glu Phe Ile Pro Phe Leu Ser Lys Leu Lys Leu Trp
    450                 455                 460
Leu His Gly Thr Pro Lys Lys Asn Cys Ile Ala Ile Val Gly Pro Pro
465                 470                 475                 480
Asp Thr Gly Lys Ser Cys Phe Cys Met Ser Leu Ile Lys Phe Leu Gly
                485                 490                 495
Gly Thr Val Ile Ser Tyr Val Asn Ser Cys Ser His Phe Trp Leu Gln
                500                 505                 510
Pro Leu Thr Asp Ala Lys Val Ala Leu Leu Asp Asp Ala Thr Gln Pro
            515                 520                 525
Cys Trp Thr Tyr Met Asp Thr Tyr Met Arg Asn Leu Leu Asp Gly Asn
    530                 535                 540
Pro Met Ser Ile Asp Arg Lys His Arg Ala Leu Thr Leu Ile Lys Cys
545                 550                 555                 560
Pro Pro Leu Leu Val Thr Ser Asn Ile Asp Ile Ser Lys Glu Glu Lys
                565                 570                 575
Tyr Lys Tyr Leu His Ser Arg Val Thr Thr Phe Thr Phe Pro Asn Pro
                580                 585                 590
Phe Pro Phe Asp Arg Asn Gly Asn Ala Val Tyr Glu Leu Ser Asp Ala
            595                 600                 605
Asn Trp Lys Cys Phe Phe Glu Arg Leu Ser Ser Ser Leu Asp Ile Glu
    610                 615                 620
Asp Ser Glu Asp Glu Glu Asp Gly Ser Asn Ser Gln Ala Phe Arg Cys
625                 630                 635                 640
Val Pro Gly Ser Val Val Arg Thr Leu
                645

<210> SEQ ID NO 4
<211> LENGTH: 649
<212> TYPE: PRT
<213> ORGANISM: Artificial Sequence
<220> FEATURE:
<223> OTHER INFORMATION: HPV6b E1 amino acid sequence including point
      mutations to remove biological activity
```

```
<400> SEQUENCE: 4

Met Ala Asp Asp Ser Gly Thr Glu Asn Glu Gly Ser Gly Cys Thr Gly
1               5                   10                  15

Trp Phe Met Val Glu Ala Ile Val Gln His Pro Thr Gly Thr Gln Ile
            20                  25                  30

Ser Asp Asp Glu Asp Glu Val Glu Asp Ser Gly Tyr Asp Met Val
            35                  40                  45

Asp Phe Ile Asp Asp Ser Asn Ile Thr His Asn Ser Leu Glu Ala Gln
        50                  55                  60

Ala Leu Phe Asn Arg Gln Glu Ala Asp Thr His Tyr Ala Thr Val Gln
65                  70                  75                  80

Asp Leu Gly Gly Lys Tyr Leu Gly Ser Pro Tyr Val Ser Pro Ile Asn
                85                  90                  95

Thr Ile Ala Glu Ala Val Glu Ser Glu Ile Ser Pro Arg Leu Asp Ala
            100                 105                 110

Ile Lys Leu Thr Arg Gln Pro Lys Lys Val Lys Arg Arg Leu Phe Gln
        115                 120                 125

Thr Arg Glu Leu Thr Asp Ser Gly Tyr Gly Tyr Ser Glu Val Glu Ala
130                 135                 140

Gly Thr Gly Thr Gln Val Glu Lys His Gly Val Pro Glu Asn Gly Gly
145                 150                 155                 160

Asp Gly Gln Glu Lys Asp Thr Gly Arg Asp Ile Glu Gly Glu His
                165                 170                 175

Thr Glu Ala Glu Ala Pro Thr Asn Ser Val Arg Glu His Ala Gly Thr
            180                 185                 190

Ala Gly Ile Leu Glu Leu Leu Lys Cys Lys Asp Leu Arg Ala Ala Leu
            195                 200                 205

Leu Gly Lys Phe Lys Glu Cys Phe Gly Leu Ser Phe Ile Asp Leu Ile
        210                 215                 220

Arg Pro Phe Lys Ser Asp Lys Thr Thr Cys Leu Asp Trp Val Val Ala
225                 230                 235                 240

Gly Phe Gly Ile His His Ser Ile Ser Glu Ala Phe Gln Lys Leu Ile
            245                 250                 255

Glu Pro Leu Ser Leu Tyr Ala His Ile Gln Trp Leu Thr Asn Ala Trp
            260                 265                 270

Gly Met Val Leu Leu Val Leu Leu Arg Phe Lys Val Asn Lys Ser Arg
        275                 280                 285

Ser Thr Val Ala Arg Thr Leu Ala Thr Leu Leu Asn Ile Pro Glu Asn
            290                 295                 300

Gln Met Leu Ile Glu Pro Pro Lys Ile Gln Ser Gly Val Ala Ala Leu
305                 310                 315                 320

Tyr Trp Phe Arg Thr Gly Ile Ser Asn Ala Ser Thr Val Ile Gly Glu
                325                 330                 335

Ala Pro Glu Trp Ile Thr Arg Gln Thr Val Ile Glu His Gly Leu Ala
            340                 345                 350

Asp Ser Gln Phe Lys Leu Thr Glu Met Val Gln Trp Ala Tyr Asp Asn
        355                 360                 365

Asp Ile Cys Glu Glu Ser Glu Ile Ala Phe Glu Tyr Ala Gln Arg Gly
370                 375                 380

Asp Phe Asp Ser Asn Ala Arg Ala Phe Leu Asn Ser Asn Met Gln Ala
385                 390                 395                 400

Lys Tyr Val Lys Asp Cys Ala Thr Met Cys Arg His Tyr Lys His Ala
                405                 410                 415
```

-continued

```
Glu Met Arg Lys Met Ser Ile Lys Gln Trp Ile Lys His Arg Gly Ser
            420                 425                 430

Lys Ile Glu Gly Thr Gly Asn Trp Lys Pro Ile Val Gln Phe Leu Arg
            435                 440                 445

His Gln Asn Ile Glu Phe Ile Pro Phe Leu Thr Lys Phe Lys Leu Trp
            450                 455                 460

Leu His Gly Thr Pro Lys Lys Asn Cys Ile Ala Ile Val Gly Pro Pro
465                 470                 475                 480

Asp Thr Asp Lys Ser Tyr Phe Cys Met Ser Leu Ile Ser Phe Leu Gly
            485                 490                 495

Gly Thr Val Ile Ser His Val Asn Ser Ser His Phe Trp Leu Gln
            500                 505                 510

Pro Leu Val Asp Ala Lys Val Ala Leu Leu Asp Asp Ala Thr Gln Pro
            515                 520                 525

Cys Trp Ile Tyr Met Asp Thr Tyr Met Arg Asn Leu Leu Asp Gly Asn
530                 535                 540

Pro Met Ser Ile Asp Arg Lys His Lys Ala Leu Thr Leu Ile Lys Cys
545                 550                 555                 560

Pro Pro Leu Leu Val Thr Ser Asn Ile Asp Ile Thr Lys Glu Asp Lys
            565                 570                 575

Tyr Lys Tyr Leu His Thr Arg Val Thr Thr Phe Thr Phe Pro Asn Pro
            580                 585                 590

Phe Pro Phe Asp Arg Asn Gly Asn Ala Val Tyr Glu Leu Ser Asn Thr
            595                 600                 605

Asn Trp Lys Cys Phe Phe Glu Arg Leu Ser Ser Ser Leu Asp Ile Gln
            610                 615                 620

Asp Ser Glu Asp Glu Asp Gly Ser Asn Ser Gln Ala Phe Arg Cys
625                 630                 635                 640

Val Pro Gly Thr Val Val Arg Thr Leu
            645
```

<210> SEQ ID NO 5
<211> LENGTH: 367
<212> TYPE: PRT
<213> ORGANISM: Human papillomavirus type 11

<400> SEQUENCE: 5

```
Met Glu Ala Ile Ala Lys Arg Leu Asp Ala Cys Gln Asp Gln Leu Leu
1               5                   10                  15

Glu Leu Tyr Glu Glu Asn Ser Ile Asp Ile His Lys His Ile Met His
            20                  25                  30

Trp Lys Cys Ile Arg Leu Glu Ser Val Leu Leu His Lys Ala Lys Gln
            35                  40                  45

Met Gly Leu Ser His Ile Gly Leu Gln Val Val Pro Pro Leu Thr Val
        50                  55                  60

Ser Glu Thr Lys Gly His Asn Ala Ile Glu Met Gln Met His Leu Glu
65                  70                  75                  80

Ser Leu Ala Lys Thr Gln Tyr Gly Val Glu Pro Trp Thr Leu Gln Asp
            85                  90                  95

Thr Ser Tyr Glu Met Trp Leu Thr Pro Pro Lys Arg Cys Phe Lys Lys
            100                 105                 110

Gln Gly Asn Thr Val Glu Val Lys Phe Asp Gly Cys Glu Asp Asn Val
            115                 120                 125

Met Glu Tyr Val Val Trp Thr His Ile Tyr Leu Gln Asp Asn Asp Ser
            130                 135                 140
```

```
Trp Val Lys Val Thr Ser Ser Val Asp Ala Lys Gly Ile Tyr Tyr Thr
145                 150                 155                 160

Cys Gly Gln Phe Lys Thr Tyr Tyr Val Asn Phe Asn Lys Glu Ala Gln
                165                 170                 175

Lys Tyr Gly Ser Thr Asn His Trp Glu Val Cys Tyr Gly Ser Thr Val
                180                 185                 190

Ile Cys Ser Pro Ala Ser Val Ser Thr Val Arg Glu Val Ser Ile
        195                 200                 205

Ala Glu Pro Thr Thr Tyr Thr Pro Ala Gln Thr Thr Ala Pro Thr Val
        210                 215                 220

Ser Ala Cys Thr Thr Glu Asp Gly Val Ser Ala Pro Pro Arg Lys Arg
225                 230                 235                 240

Ala Arg Gly Pro Ser Thr Asn Asn Thr Leu Cys Val Ala Asn Ile Arg
                245                 250                 255

Ser Val Asp Ser Thr Ile Asn Asn Ile Val Thr Asp Asn Tyr Asn Lys
                260                 265                 270

His Gln Arg Arg Asn Asn Cys His Ser Ala Ala Thr Pro Ile Val Gln
                275                 280                 285

Leu Gln Gly Asp Ser Asn Cys Leu Lys Cys Phe Arg Tyr Arg Leu Asn
        290                 295                 300

Asp Lys Tyr Lys His Leu Phe Glu Leu Ala Ser Ser Thr Trp His Trp
305                 310                 315                 320

Ala Ser Pro Glu Ala Pro His Lys Asn Ala Ile Val Thr Leu Thr Tyr
                325                 330                 335

Ser Ser Glu Glu Gln Arg Gln Gln Phe Leu Asn Ser Val Lys Ile Pro
                340                 345                 350

Pro Thr Ile Arg His Lys Val Gly Phe Met Ser Leu His Leu Leu
                355                 360                 365

<210> SEQ ID NO 6
<211> LENGTH: 368
<212> TYPE: PRT
<213> ORGANISM: Human papillomavirus type 6a

<400> SEQUENCE: 6

Met Glu Ala Ile Ala Lys Arg Leu Asp Ala Cys Gln Glu Gln Leu Leu
1               5                   10                  15

Glu Leu Tyr Glu Glu Asn Ser Thr Asp Leu Asn Lys His Val Leu His
                20                  25                  30

Trp Lys Cys Met Arg His Glu Ser Val Leu Leu Tyr Lys Ala Lys Gln
                35                  40                  45

Met Gly Leu Ser His Ile Gly Met Gln Val Val Pro Pro Leu Lys Val
        50                  55                  60

Ser Glu Ala Lys Gly His Asn Ala Ile Glu Met Gln Met His Leu Glu
65                  70                  75                  80

Ser Leu Leu Lys Thr Glu Tyr Ser Met Glu Pro Trp Thr Leu Gln Glu
                85                  90                  95

Thr Ser Tyr Glu Met Trp Gln Thr Pro Pro Lys Arg Cys Phe Lys Lys
                100                 105                 110

Arg Gly Lys Thr Val Glu Val Lys Phe Asp Gly Cys Ala Asn Asn Thr
                115                 120                 125

Met Asp Tyr Val Val Trp Thr Asp Val Tyr Val Gln Asp Thr Asp Ser
        130                 135                 140

Trp Val Lys Val His Ser Met Val Asp Ala Lys Gly Ile Tyr Tyr Thr
145                 150                 155                 160
```

Cys Gly Gln Phe Lys Thr Tyr Tyr Val Asn Phe Val Lys Glu Ala Glu
                165                 170                 175

Lys Tyr Gly Ser Thr Lys Gln Trp Glu Val Cys Tyr Gly Ser Thr Val
            180                 185                 190

Ile Cys Ser Pro Ala Ser Val Ser Thr Thr Gln Glu Val Ser Ile
        195                 200                 205

Pro Glu Ser Thr Thr Tyr Thr Pro Ala Gln Thr Ser Thr Pro Val Ser
    210                 215                 220

Ser Ser Thr Gln Glu Asp Ala Val Gln Thr Pro Pro Arg Lys Arg Ala
225                 230                 235                 240

Arg Gly Val Gln Gln Ser Pro Cys Asn Ala Leu Cys Val Ala His Ile
                245                 250                 255

Gly Pro Val Asp Ser Gly Asn His Asn Leu Ile Thr Asn Asn His Asp
            260                 265                 270

Gln His Gln Arg Arg Asn Asn Ser Asn Ser Ser Ala Thr Pro Ile Val
        275                 280                 285

Gln Phe Gln Gly Glu Ser Asn Cys Leu Lys Cys Phe Arg Tyr Arg Leu
    290                 295                 300

Asn Asp Lys His Arg His Leu Phe Asp Leu Ile Ser Ser Thr Trp His
305                 310                 315                 320

Trp Ala Ser Pro Lys Ala Pro His Lys His Ala Ile Val Thr Val Thr
                325                 330                 335

Tyr His Ser Glu Glu Gln Arg Gln Gln Phe Leu Asn Val Val Lys Ile
            340                 345                 350

Pro Pro Thr Ile Arg His Lys Leu Gly Phe Met Ser Leu His Leu Leu
        355                 360                 365

<210> SEQ ID NO 7
<211> LENGTH: 368
<212> TYPE: PRT
<213> ORGANISM: Human papillomavirus type 6b

<400> SEQUENCE: 7

Met Glu Ala Ile Ala Lys Arg Leu Asp Ala Cys Gln Glu Gln Leu Leu
 1               5                  10                  15

Glu Leu Tyr Glu Glu Asn Ser Thr Asp Leu His Lys His Val Leu His
            20                  25                  30

Trp Lys Cys Met Arg His Glu Ser Val Leu Leu Tyr Lys Ala Lys Gln
        35                  40                  45

Met Gly Leu Ser His Ile Gly Met Gln Val Val Pro Pro Leu Lys Val
    50                  55                  60

Ser Glu Ala Lys Gly His Asn Ala Ile Glu Met Gln Met His Leu Glu
65                  70                  75                  80

Ser Leu Leu Arg Thr Glu Tyr Ser Met Glu Pro Trp Thr Leu Gln Glu
                85                  90                  95

Thr Ser Tyr Glu Met Trp Gln Thr Pro Pro Lys Arg Cys Phe Lys Lys
            100                 105                 110

Arg Gly Lys Thr Val Glu Val Lys Phe Asp Gly Cys Ala Asn Asn Thr
        115                 120                 125

Met Asp Tyr Val Val Trp Thr Asp Val Tyr Val Gln Asp Asn Asp Thr
    130                 135                 140

Trp Val Lys Val His Ser Met Val Asp Ala Lys Gly Ile Tyr Tyr Thr
145                 150                 155                 160

Cys Gly Gln Phe Lys Thr Tyr Tyr Val Asn Phe Val Lys Glu Ala Glu
                165                 170                 175

-continued

```
Lys Tyr Gly Ser Thr Lys His Trp Glu Val Cys Tyr Gly Ser Thr Val
            180                 185                 190

Ile Cys Ser Pro Ala Ser Val Ser Ser Thr Thr Gln Glu Val Ser Ile
            195                 200                 205

Pro Glu Ser Thr Thr Tyr Thr Pro Ala Gln Thr Thr Leu Val Ser
            210                 215                 220

Ser Ser Thr Lys Glu Asp Ala Val Gln Thr Pro Pro Arg Lys Arg Ala
225                 230                 235                 240

Arg Gly Val Gln Gln Ser Pro Cys Asn Ala Leu Cys Val Ala His Ile
                245                 250                 255

Gly Pro Val Asp Ser Gly Asn His Asn Leu Ile Thr Asn Asn His Asp
            260                 265                 270

Gln His Gln Arg Arg Asn Asn Ser Asn Ser Ser Ala Thr Pro Ile Val
            275                 280                 285

Gln Phe Gln Gly Glu Ser Asn Cys Leu Lys Cys Phe Arg Tyr Arg Leu
            290                 295                 300

Asn Asp Arg His Arg His Leu Phe Asp Leu Ile Ser Ser Thr Trp His
305                 310                 315                 320

Trp Ala Ser Ser Lys Ala Pro His Lys His Ala Ile Val Thr Val Thr
                325                 330                 335

Tyr Asp Ser Glu Glu Gln Arg Gln Gln Phe Leu Asp Val Val Lys Ile
            340                 345                 350

Pro Pro Thr Ile Ser His Lys Leu Gly Phe Met Ser Leu His Leu Leu
            355                 360                 365

<210> SEQ ID NO 8
<211> LENGTH: 367
<212> TYPE: PRT
<213> ORGANISM: Artificial Sequence
<220> FEATURE:
<223> OTHER INFORMATION: HPV11 E2 aminio acid sequence including a point
      mutation to remove biological activity

<400> SEQUENCE: 8

Met Glu Ala Ile Ala Lys Arg Leu Asp Ala Cys Gln Asp Gln Leu Leu
1               5                   10                  15

Glu Leu Tyr Glu Glu Asn Ser Ile Asp Ile His Lys His Ile Met His
            20                  25                  30

Trp Lys Cys Ile Arg Leu Glu Ser Val Leu Leu His Lys Ala Lys Gln
        35                  40                  45

Met Gly Leu Ser His Ile Gly Leu Gln Val Val Pro Pro Leu Thr Val
    50                  55                  60

Ser Glu Thr Lys Gly His Asn Ala Ile Glu Met Gln Met His Leu Glu
65                  70                  75                  80

Ser Leu Ala Lys Thr Gln Tyr Gly Val Glu Pro Trp Thr Leu Gln Asp
                85                  90                  95

Thr Ser Tyr Glu Met Trp Leu Thr Pro Pro Lys Arg Cys Phe Ala Lys
            100                 105                 110

Gln Gly Asn Thr Val Glu Val Lys Phe Asp Gly Cys Glu Asp Asn Val
        115                 120                 125

Met Glu Tyr Val Val Trp Thr His Ile Tyr Leu Gln Asp Asn Asp Ser
    130                 135                 140

Trp Val Lys Val Thr Ser Ser Val Asp Ala Lys Gly Ile Tyr Tyr Thr
145                 150                 155                 160

Cys Gly Gln Phe Lys Thr Tyr Tyr Val Asn Phe Asn Lys Glu Ala Gln
                165                 170                 175
```

```
Lys Tyr Gly Ser Thr Asn His Trp Glu Val Cys Tyr Gly Ser Thr Val
            180                 185                 190

Ile Cys Ser Pro Ala Ser Val Ser Ser Thr Val Arg Glu Val Ser Ile
            195                 200                 205

Ala Glu Pro Thr Thr Tyr Thr Pro Ala Gln Thr Thr Ala Pro Thr Val
            210                 215                 220

Ser Ala Cys Thr Thr Glu Asp Gly Val Ser Ala Pro Pro Arg Lys Arg
225                 230                 235                 240

Ala Arg Gly Pro Ser Thr Asn Asn Thr Leu Cys Val Ala Asn Ile Arg
                245                 250                 255

Ser Val Asp Ser Thr Ile Asn Asn Ile Val Thr Asp Asn Tyr Asn Lys
                260                 265                 270

His Gln Arg Arg Asn Asn Cys His Ser Ala Ala Thr Pro Ile Val Gln
                275                 280                 285

Leu Gln Gly Asp Ser Asn Cys Leu Lys Cys Phe Arg Tyr Arg Leu Asn
            290                 295                 300

Asp Lys Tyr Lys His Leu Phe Glu Leu Ala Ser Ser Thr Trp His Trp
305                 310                 315                 320

Ala Ser Pro Glu Ala Pro His Lys Asn Ala Ile Val Thr Leu Thr Tyr
                325                 330                 335

Ser Ser Glu Glu Gln Arg Gln Gln Phe Leu Asn Ser Val Lys Ile Pro
                340                 345                 350

Pro Thr Ile Arg His Lys Val Gly Phe Met Ser Leu His Leu Leu
                355                 360                 365

<210> SEQ ID NO 9
<211> LENGTH: 368
<212> TYPE: PRT
<213> ORGANISM: Artificial Sequence
<220> FEATURE:
<223> OTHER INFORMATION: HPV6b E2 amino acid sequence including a point
      mutation to remove biological activity

<400> SEQUENCE: 9

Met Glu Ala Ile Ala Lys Arg Leu Asp Ala Cys Gln Glu Gln Leu Leu
 1               5                  10                  15

Glu Leu Tyr Glu Glu Asn Ser Thr Asp Leu His Lys His Val Leu His
            20                  25                  30

Trp Lys Cys Met Arg His Glu Ser Val Leu Leu Tyr Lys Ala Lys Gln
            35                  40                  45

Met Gly Leu Ser His Ile Gly Met Gln Val Val Pro Pro Leu Lys Val
        50                  55                  60

Ser Glu Ala Lys Gly His Asn Ala Ile Glu Met Gln Met His Leu Glu
65                  70                  75                  80

Ser Leu Leu Arg Thr Glu Tyr Ser Met Glu Pro Trp Thr Leu Gln Glu
                85                  90                  95

Thr Ser Tyr Glu Met Trp Gln Thr Pro Pro Lys Arg Cys Phe Ala Lys
            100                 105                 110

Arg Gly Lys Thr Val Glu Val Lys Phe Asp Gly Cys Ala Asn Asn Thr
            115                 120                 125

Met Asp Tyr Val Val Trp Thr Asp Val Tyr Val Gln Asp Asn Asp Thr
        130                 135                 140

Trp Val Lys Val His Ser Met Val Asp Ala Lys Gly Ile Tyr Tyr Thr
145                 150                 155                 160

Cys Gly Gln Phe Lys Thr Tyr Tyr Val Asn Phe Val Lys Glu Ala Glu
                165                 170                 175
```

```
Lys Tyr Gly Ser Thr Lys His Trp Glu Val Cys Tyr Gly Ser Thr Val
            180                 185                 190

Ile Cys Ser Pro Ala Ser Val Ser Thr Thr Gln Glu Val Ser Ile
        195                 200                 205

Pro Glu Ser Thr Thr Tyr Thr Pro Ala Gln Thr Thr Leu Val Ser
        210                 215                 220

Ser Ser Thr Lys Glu Asp Ala Val Gln Thr Pro Pro Arg Lys Arg Ala
225                 230                 235                 240

Arg Gly Val Gln Gln Ser Pro Cys Asn Ala Leu Cys Val Ala His Ile
                245                 250                 255

Gly Pro Val Asp Ser Gly Asn His Asn Leu Ile Thr Asn Asn His Asp
            260                 265                 270

Gln His Gln Arg Arg Asn Asn Ser Asn Ser Ser Ala Thr Pro Ile Val
        275                 280                 285

Gln Phe Gln Gly Glu Ser Asn Cys Leu Lys Cys Phe Arg Tyr Arg Leu
        290                 295                 300

Asn Asp Arg His Arg His Leu Phe Asp Leu Ile Ser Ser Thr Trp His
305                 310                 315                 320

Trp Ala Ser Ser Lys Ala Pro His Lys His Ala Ile Val Thr Val Thr
                325                 330                 335

Tyr Asp Ser Glu Glu Gln Arg Gln Gln Phe Leu Asp Val Val Lys Ile
            340                 345                 350

Pro Pro Thr Ile Ser His Lys Leu Gly Phe Met Ser Leu His Leu Leu
            355                 360                 365

<210> SEQ ID NO 10
<211> LENGTH: 1965
<212> TYPE: DNA
<213> ORGANISM: Artificial Sequence
<220> FEATURE:
<223> OTHER INFORMATION: Codon optimised and mutated nucleotide sequence
      for HPV6b E1

<400> SEQUENCE: 10
gcggccgcca tggcagacga ttccggtact gagaacgaag ttctggttg taccggttgg      60 ttcatggttg aagcaatcgt tcagcatccg actggtaccc agatctccga tgacgaagac     120
gaagaagttg aagattctgg ttacgacatg gttgacttca tcgatgactc caacatcact     180
cataactctc tggaagcaca ggctctgttt aaccgccagg aagctgatac ccattacgct     240
actgttcagg acctgggagg caaatatctg gctctccgt acgttccc gatcaacact      300 atcgcagaag cagttgagtc tgaaatctcc ccgcgcctgg acgctatcaa actgactcgt     360
cagccgaaga ggttaaacg tcgtctgttc cagactcgtg aactgaccga ctccggttac     420
ggttatagcg aagttgaggc tggcaccggc acccaggttg aaaaacacgg tgtaccggaa     480
aacggcggcg acgtcagga aaaggacacc ggccgcgaca tcgagggtga ggaacacacc     540
gaagctgaag ctccgactaa ctctgttcgt gaacacgcag gtactgcggg tatcctggaa     600
ctgctgaaat gcaaagacct cgcgcggct ctgctgggca aattcaaaga atgcttcggc     660
ctgtctttca ttgacctgat ccgtccgttt aagtctgaca aaactacctg tctggactgg     720
gttgtagcag gcttcggcat ccaccactct atctctgaag cattccagaa actgatcgag     780
ccgctgtctc tgtacgcgca catccagtgg ctgactaacg cttggggtat ggttctgctg     840
gtactgctgc gctttaaagt aaacaaatct cgttccactg ttgctcgtac tctggctacc     900
ctgctgaaca tcccggagaa ccagatgctg atcgaaccgc gaaaatcca gtctggtgta     960
```

-continued

```
gctgcactgt actggtttcg tactggcatc tctaacgcta gcactgttat cggtgaagca   1020
ccggaatgga tcactcgtca gaccgttatc gaacacggtc tggcagattc tcagttcaaa   1080
ctgactgaaa tggttcagtg gcatacgac aacgacatct gcgaggaatc tgaaattgcg    1140
ttcgaatacg ctcagcgtgg cgacttcgac tccaacgctc gtgctttcct gaacagcaac   1200
atgcaggcta atacgtaaa agactgcgct accatgtgcc gtcactacaa acacgcggaa    1260
atgcgtaaaa tgtctatcaa acagtggatc aagcaccgcg gttctaaaat cgaaggtacc   1320
ggtaactgga aaccgatcgt tcagttcctg cgccatcaga acatcgaatt catcccgttc   1380
ctgaccaaat tcaagctgtg gctgcacggt accccgaaaa aaactgcat cgctatcgta    1440 ggtccaccgg acactgacaa gtcttacttc tgtatgtccc tgatctcttt cctgggcggc   1500
actgtaatct ctcacgttaa ctcttcctcc catttctggc tgcagccact ggtagacgcg   1560
aaagtagctc tgctggacga cgcgacccag ccgtgctgga tctacatgga tacttacatg   1620
cgcaacctgc tggacggtaa cccgatgtct atcgaccgta acacaaagc gctgactctg    1680 atcaagtgcc gccgctgct ggtaacttct aacatcgaca tcaccaagga agataaatac     1740
aagtacctgc atacccgtgt tactaccttt actttcccga acccgttccc gtttgatcgt   1800
aacggtaacg ctgtttacga actgtccaac actaactgga aatgcttctt cgagcgtctg   1860
tcttcctccc tggacatcca ggactctgaa gatgaagaag atggttctaa ctctcaggct   1920
ttccgttgtg ttccgggtac tgttgttcgt actctgtgag gatcc                   1965
```

<210> SEQ ID NO 11
<211> LENGTH: 1119
<212> TYPE: DNA
<213> ORGANISM: Artificial Sequence
<220> FEATURE:
<223> OTHER INFORMATION: Codon optimised and mutated nucleotide sequence for HPV11 E2

<400> SEQUENCE: 11

```
gcggccgcca tggaagccat cgcgaagagg ctcgacgcct gccaggacca gctgctcgag   60
ctgtacgagg agaacagcat tgacatccat aagcacatca tgcactggaa gtgcattcgc   120
ctggagagcg tgctgttgca aaggccaag cagatgggcc tgtcccacat aggccttcag    180
gtggtccccc ctctgaccgt gtcagagaca aagggccata cgcaatcga gatgcagatg    240 cacctcgagt cgctggcgaa aacacagtac ggcgtggagc catggaccct gcaggacacc   300
tcgtacgaaa tgtggctgac cccacctaag cgatgcttcg ccaaacaggg caacacagtg   360
gaggtgaagt cgacggctg tgaggataac gttatggagt atgtcgtgtg gacgcacatc   420
tatctgcagg acaacgacag ttgggtgaag gtgaccagct ccgtggacgc gaagggcatc   480
tactatacct gtgggcagtt taaaacctac tatgtgaact tcaacaaaga ggcccaaaag   540
tatggctcca ccaaccactg ggaggtctgc tatgggagca cggtgatttg ctctcccgcc   600
agcgtgtcta gcactgtgcg cgaggtgagc attgccgagc cgaccacgta caccctgcc    660 cagacgaccg ctccgaccgt gtctgcttgt actaccgagg acggcgtgag cgctccaccc   720
aggaagcgtg cgaggggccc aagcaccaac aacaccctct gtgtggcgaa cattcgcagc   780
gtcgacagta ccatcaataa catcgtgacg gataactata caagcacca gaggcgtaac    840 aactgtcact ctgccgcaac ccccatcgtg cagctccagg agacagcaa ttgccttaag   900 tgcttccgct atcgcctcaa cgacaagtac aagcacctct ttgagctcgc ctcgtcgacg   960
tggcactggg cctcacccga ggcacctcac aagaacgcca tcgtcactct cacttactcc   1020
```

| agtgaggagc agagacagca gtttctgaac agcgtgaaga tcccaccgac gatccgtcat | 1080 |
|---|---|
| aaggtcggct tcatgtcact gcatctcctg tgaggatcc | 1119 |

```
<210> SEQ ID NO 12
<211> LENGTH: 45
<212> TYPE: DNA
<213> ORGANISM: Artificial Sequence
<220> FEATURE:
<223> OTHER INFORMATION: Oligonucleotide linker

<400> SEQUENCE: 12
```

| agcttgcggc cgctagcgat atcggtacca tatgtcgacg gatcc | 45 |
|---|---|

```
<210> SEQ ID NO 13
<211> LENGTH: 45
<212> TYPE: DNA
<213> ORGANISM: Artificial Sequence
<220> FEATURE:
<223> OTHER INFORMATION: Oligonucleotide linker

<400> SEQUENCE: 13
```

| ggccggatcc gtcgacatct ggtaccgata tcgctagcgg ccgca | 45 |
|---|---|

```
<210> SEQ ID NO 14
<211> LENGTH: 23
<212> TYPE: PRT
<213> ORGANISM: Human papillomavirus type 6b

<400> SEQUENCE: 14
```

Cys Ser Ser Ser Leu Asp Ile Gln Asp Ser Glu Asp Glu Glu Asp Gly
1               5                   10                  15

Ser Asn Ser Gln Ala Phe Arg
            20

```
<210> SEQ ID NO 15
<211> LENGTH: 22
<212> TYPE: PRT
<213> ORGANISM: Human papillomavirus type 6b

<400> SEQUENCE: 15
```

Met Glu Ala Ile Ala Lys Arg Leu Asp Ala Cys Gln Glu Gln Leu Leu
1               5                   10                  15

Glu Leu Tyr Glu Glu Cys
            20

```
<210> SEQ ID NO 16
<211> LENGTH: 45
<212> TYPE: DNA
<213> ORGANISM: Homo sapien

<400> SEQUENCE: 16
```

| agcttgcggc cgctagcgat atcggtacca tatgtcgacg gatcc | 45 |
|---|---|

```
<210> SEQ ID NO 17
<211> LENGTH: 45
<212> TYPE: DNA
<213> ORGANISM: Homo sapien

<400> SEQUENCE: 17
```

| acgccggcga tcgctatagc catggtctac agctgcctag gccgg | 45 |
|---|---|

```
<210> SEQ ID NO 18
<211> LENGTH: 23
<212> TYPE: PRT
<213> ORGANISM: Oryctolagus cuniculus

<400> SEQUENCE: 18

Cys Ser Ser Ser Leu Asp Ile Gln Asp Ser Glu Asp Glu Glu Asp Gly
  1               5                  10                  15

Ser Asn Ser Gln Ala Phe Arg
             20

<210> SEQ ID NO 19
<211> LENGTH: 22
<212> TYPE: PRT
<213> ORGANISM: Human papillomavirus type 6b

<400> SEQUENCE: 19

Met Glu Ala Ile Ala Lys Arg Leu Asp Ala Cys Gln Glu Gln Leu Leu
  1               5                  10                  15

Glu Leu Tyr Glu Glu Cys
             20

<210> SEQ ID NO 20
<211> LENGTH: 16
<212> TYPE: PRT
<213> ORGANISM: Oryctolagus cuniculus

<400> SEQUENCE: 20

Met Ala Ala Arg Lys Gly Thr Asp Ser Glu Thr Glu Asp Gly Gly Cys
  1               5                  10                  15

<210> SEQ ID NO 21
<211> LENGTH: 20
<212> TYPE: PRT
<213> ORGANISM: Oryctolagus cuniculus

<400> SEQUENCE: 21

Cys Lys His Leu Asp Leu Ser Asp Pro Glu Asp Gly Glu Asp Gly Glu
  1               5                  10                  15

Thr Gln Arg Gly
             20
```

The invention claimed is:

1. A method of expressing a human papillomavirus (HPV) polypeptide in a mammalian cell comprising:
   delivering a codon-optimized polynucleotide encoding an HPV polypeptide to a cell of a mammalian species, said polynucleotide having a codon usage pattern that resembles the codon usage pattern of highly expressed genes of a mammalian species and a codon usage coefficient of greater than 0.5 but less than 1.0,
   whereby said encoded polypeptide is expressed by the cell.

2. The method of claim 1 wherein the mammalian cell is a human cell.

3. The method of claim 1 wherein the HPV polypeptide comprises an HPV early protein or fragment or derivative thereof.

4. The method of claim 3 wherein the early protein is a member selected from the group consisting of E1, E2 and E7.

5. The method of claim 3 wherein the polypeptide comprises more than one HPV early protein.

6. The method of claim 1 wherein the HPV polypeptide is from at least one member selected from the group consisting of HPV 6a, HPV 6b, HPV 11, HPV 16, HPV 18, HPV 33 or HPV 45.

7. The method of claim 6 wherein the HPV polypeptide is from at least one member selected from the group consisting of HPV 6a, HPV6b and HPV11.

8. The method of claim 7 wherein the HPV polypeptide is an E2 protein.

9. The method of claim 1, wherein said mammalian species is human.

10. A method for preventing or treating an HPV infection in a human, or a symptom or disease associated with said HPV infection, comprising administering to a human a codon-optimized polynucleotide encoding an HPV polypeptide having a codon usage pattern that resembles the codon usage pattern of highly expressed human genes and a codon usage coefficient of greater than 0.5 but less than 1.

11. The method of claim 10 wherein the polynucleotide is provided in the form of a vector.

12. The method of claim 11 wherein the vector is a plasmid.

13. The method of claim 11 wherein the vector is a viral vector.

14. The method of claim 10 wherein the polynucleotide is administered by needle injection.

15. The method of claim 10 wherein the polynucleotide is administered by particle-mediated DNA delivery.

16. The method of claim 10 wherein the polynucleotide is administered topically.

* * * * *